(12) United States Patent
Trower et al.

(10) Patent No.: US 11,591,346 B2
(45) Date of Patent: Feb. 28, 2023

(54) METHOD OF TREATMENT OF SYMPTOMS OF MENOPAUSE

(71) Applicant: KaNDy Therapeutics Limited, Stevenage (GB)

(72) Inventors: Mike Trower, Stevenage (GB); Monica Lazaro, St. Petersburg, FL (US); Derek Bush, St. Petersburg, FL (US); David Elder, Hertford (GB); Mary Kerr, Stevenage (GB)

(73) Assignee: KaNDy Therapeutics Limited, Stevenage (GB)

(*) Notice: Subject to any disclaimer, the term of this patent is extended or adjusted under 35 U.S.C. 154(b) by 91 days.

(21) Appl. No.: 16/984,961

(22) Filed: Aug. 4, 2020

(65) Prior Publication Data
US 2020/0361956 A1  Nov. 19, 2020

Related U.S. Application Data

(62) Division of application No. 16/351,659, filed on Mar. 13, 2019, now Pat. No. 10,774,091.

(60) Provisional application No. 62/642,622, filed on Mar. 14, 2018.

(51) Int. Cl.
| C07D 498/04 | (2006.01) |
| A61P 15/00 | (2006.01) |
| A61K 31/5383 | (2006.01) |

(52) U.S. Cl.
CPC ........ *C07D 498/04* (2013.01); *A61K 31/5383* (2013.01); *A61P 15/00* (2018.01); *C07B 2200/13* (2013.01)

(58) Field of Classification Search
CPC ... C07D 498/04; C07B 2200/13; A61P 15/00; A61K 31/5385
See application file for complete search history.

(56) References Cited

U.S. PATENT DOCUMENTS

| 7,683,056 B2 ‡ | 3/2010 | Alvaro | C07D 487/04 514/230.5 |
| 8,093,242 B2 | 1/2012 | Anderton et al. | |
| 8,796,269 B2 * | 8/2014 | Craig | A61P 25/18 514/249 |
| 10,195,205 B2 * | 2/2019 | Trower | A61K 31/444 |
| 2002/0016283 A1 | 2/2002 | Guttuso | |
| 2003/0092602 A1 ‡ | 5/2003 | Leach et al. | A61K 31/4545 514/1 |
| 2005/0110987 A1 | 5/2005 | Furman et al. | |
| 2006/0014818 A1 | 1/2006 | Paulini et al. | |
| 2012/0028980 A1 | 2/2012 | Boscan et al. | |
| 2012/0157450 A1 | 6/2012 | Craig et al. | |
| 2013/0338180 A1 ‡ | 12/2013 | Parvataneni | A61K 9/4858 514/275 |
| 2016/0339037 A1 ‡ | 11/2016 | Trower | A61K 31/436 |

FOREIGN PATENT DOCUMENTS

| EP | 1192952 A2 | 4/2002 |
| WO | 2000059873 A1 | 10/2000 |
| WO | 2001095904 A1 | 12/2001 |
| WO | 2002089802 A2 | 11/2002 |
| WO | 2002089802 A3 | 5/2003 |
| WO | 2004056799 A2 | 7/2004 |
| WO | 2004056805 A1 | 7/2004 |
| WO | 2005002577 A1 | 1/2005 |
| WO | 2005097774 A1 | 10/2005 |
| WO | 2005097794 A1 | 10/2005 |
| WO | 2005110987 A1 | 11/2005 |
| WO | 2006013050 A1 | 2/2006 |
| WO | 2006013205 A1 | 2/2006 |
| WO | 2007028654 A1 | 3/2007 |
| WO | 2008128891 A1 | 10/2008 |
| WO | 2011023733 A1 | 3/2011 |
| WO | 2011131571 A1 | 10/2011 |
| WO | 2012020162 A1 | 2/2012 |
| WO | 2014089019 A1 | 6/2014 |
| WO | 2015033163 A1 | 3/2015 |

OTHER PUBLICATIONS

International Search Report and Written Opinion of PCT/EP2019/056303 dated Jun. 14, 2019.‡
Page, et al., "Excessive placental secretion of neurokinin B during the third trimester causes pre-eclampsia," Nature, vol. 405, Jun. 15, 2000, pp. 797-800.
Page, et al., "Gene regulation of neurokinin B and its receptor NK3 in late pregnancy and pre-eclampsia," Molecular Human Reproduction, vol. 12, No. 7, pp. 427-433, 2006.
Page, N.M., "Neurokinin B and pre-eclampsia: a decade of discovery," Reproductive Biology and Endocrinology 2010, 8:4.
Panocka et al., "Antidepressant-type effect of the NK3 tachykinin receptor agonist aminosenktide in mouse lines differing in endogenous opioid system activity," Peptides 22(7): 1037-42 (2001).
Patacchini et al., "tachykinin NK1 and NK2 receptors mediate inhitibory vs excitatory motor responses in human isolated corpus cavernosum and spongiosum," Br J. Pharmacol.. 135(6):1351-4 (2002).
Patak E., et al, "Tachykinins and tachykinin receptors in human uterus", British Journal of Pharmacology, (2003) 139, 523-532.
Patak E., et a., "Funcltional and molecular characterization of tachykinins and tachykinin receptors in the mouse uterus", Biology of Reproduction 72, 1125-1133 (2005).
Patak, et al., "Functional and molecular characterization of tachykinins and tachykinin receptors in the mouse uterus," Biology of Reproduction, 72, 1125-1133 (2005).

(Continued)

*Primary Examiner* — Timothy R Rozof
(74) *Attorney, Agent, or Firm* — Morrison & Foerster LLP

(57) ABSTRACT

The present invention generally relates to novel pharmaceutical formulations containing 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide, methods of preparation thereof and their use in medical therapy.

34 Claims, 1 Drawing Sheet

(56) References Cited

OTHER PUBLICATIONS

Paul et al., "How to Improve R&D Productivity: The Pharmaceutical Industry's Grand Challenge," Nature Review/Drug Discovery 9:203-214 (2010).
Peters, et al., "Discovery of potent, balanced and orally active dual NK1/NK3 receptor ligands," Bioorganic & Medicinal Chemistry Letters 20 (2010) 3405-3408.
Pinkerton et al., "Relief of vasomotor symptoms with the tissue-selective estrogen complex containing bazedoxifene/conjugated estrogens: a randomized, controlled trial," Menopause. 16(6):1116-24 (2009).
Pintado, et al., "A role for tachykinins in female mouse and rat reproductive function," Biology of Reproduction, 69, 940-946 (2003).
Pinto FM, et al., "Ovarian steroids regulate tachykinin and tachykinin receptor gene expression in the mouse uterus", Reproductive Biology and Endocrinology 2009, 7:77.
Porter, et al., "Neurokinin-3 receptor activation in the retrochiasmatic area is essential for the full pre-ovulatory uteinising hormone surge in ewes," J Neuroendocrinol Nov. 2014; 26(11):776-784.
Press Release: KaNDy Therapeutics launched to advance a breakthrough treatment in Women's Health, Sep. 27, 2017.
Ramalho, et al., "Substance P antagonist improves both obesity and asthma in a mouse model," Allergy 2013 68:48-54.
Ramaswamy, et al., "Neurokinin B stimulates GnRH release in the male monkey (*Macaca mulatta*) and is colocalized with kisspeptin in the arcuate nucleus," Endocrinology, 151:4494-4503, 2010.
Rameshwar & Gascon, "Hematopoietic modulation by the tachykinins," Acta Haematol. 98(2):59-64 (1997).
Rance Ne, et al., "Hypertrophy and increased gene expression of neurons containing neurokinin-B and substance-P messenger ribonucleic acids in the hypothalami of postmenopausal women", Endocrinology, 128: 2239-2247, 1991.
Rance, et al., "Modulation of body temperature and LH secretion by hypothalamic KNDy (kisspeptin, neurokinin B and dynorphin) neurons: a novel hypothesis on the mechanism of hot flushes," Frontiers in Neuroendocrinology 34 (2013) 211-227.
Rance, et al., "Neurokinin B and the hypothalamic regulation of reproduction," Brain Res. Dec. 10, 2010; 1364: 116-128.
Rance, et al.,"Postmenopausal hypertrophy of neurons expressing the estrogen receptor gene in the human hypothalamus," JCE & M 1990 Vol. 71, No. 1, pp. 79-85.
Rance, N.E., "Menopause and the human hypothalamus: evidence for the role of kisspeptin/neurokinin B neurons in the regulation of estrogen negative feedback," Peptides 30 (2009) 111-122.
Regoli et al., "Neuropeptides {Neurokinins, Bombesin, Neurotensin, Cholecystokinins, Opioids) and Smooth Muscle," in Pharmacology of Smooth Muscle, Szekeres & Papp {ed.), Springer-Verlag {Heidelberg, 1994).
Renner, et al., "Neurokinin 1 receptor gene polymorphism might be correlated with recurrence rates in endometriosis," Gynecological Endocrinology, Nov. 2009; 25(11):726-733.
Ribeiro et al., "Tachykinin NK{3)receptor involvement in anxiety," Neuropeptides 33(2):181-8 (1999).
Ridler, et al., "Characterising the plasma-target occupancy relationship of the neurokinin antagonist GSK1144814 with PET," J Psychopharmacol 2014 vol. XX(X) 1-10.
Rometo, et al., "Changes in prodynorphin gene expression and neuronal morphology in the hypothalamus of postmenopausal women," J Neuroendocrinol. Dec. 2008; 20(12):1376-1381.
Rotterdam eESHRE/ASRM-Sponsored PCOS Consensun Workshop Group, "Revised 2003 consensus on diagnostic criteria and long-term health risks related to polycystic ovary syndrome," Fertility and Sterility, vol. 81, No. 1, Jan. 2004, 19-25.
Ruiz-Pino, et al., "Neurokinin B and the control of the gonadotropic axis in the rat: developmental changes, sexual dimorphism, and regulation by gonadal steroids," Endocrinology 153:4818-4829, 2012.
Ruka, et al., "Regulation of arcuate neurons coexpressing kisspeptin, neurokinin B, and dynorphin by modulators of neurokinin 3 and κ-opioid receptors in adult male mice," Endocrinology 154:2761-2771, 2013.
Rumsey and Kerns, "Combined Tachykinin NK1, NK2, and NK3 Receptor Antagonists," in Tachykinins, Holzer (ed.), Springer-Verlag (Heidelberg, 2004).
Sandoval-Guzman, et al., "Effects of ovariectomy on the neuroendocrine axes regulating reproduction and energy balance in young cynomolgus macaques," Journal of Neuroendocrinology, 2004, vol. 16, 146-153.
Sarcia-Recio and Gascon, "Biological and Pharmacological Aspects of the NK1-Receptor," Biomed Res Int 2015:495704 (2015).
Savoie et al., "Involvement of NK1 and NK2 Receptors in Pulmonary Responses Elicited by Non-Adrenergic, Non-Cholinergic Vagal Stimulation in Guinea-Pigs," J_ Pharm.Pharmacol. 47:914-920 (1995).
Scholzen et al., "Cutaneous allergic contact dermatitis responses are diminished in mice deficient in neurokinin 1 receptors and augmented by neurokinin 2 receptor blockage," FASEB J_ 18(9):1007-9 (2004).
Schwarz & Ackenheil, "The role of substance P in depression: therapeutic implications," Dialogues Clin Neurosci. 4(1):21-9 (2002).
Search Report and Written Opinion of PCT/EP2016/060945 dated Jun. 29, 2016.
Semple, et al., "The recent genetics of hypogonadotrophic hypogonadism—novel insights and new questions insights and new questions," Clinical Endocrinology (2010 72, 427-435.
Simon et al., "Low-dose paroxetine 7.5 mg for menopausal vasomotor symptoms: Two randomized controlled trials," Menopause: The Journal of The North American Menopause Society 20(10):1027-1035 (2013).
Skorupskaite, et al., "Role of a neurokinin B receptor antagonist in the regulation of ovarian function in healthy women," Poster Abstract, Published online on Feb. 26, 2015.
Skrapis K, et al., "Neuropeptide co-expression in hypothalamic kisspeptin neurons of laboratory animals and the human". Frontiers in Neuroscience Feb. 2015, vol. 9, Article 29 1-9.
Skrupsakite, et al., "The kisspeptin-GnRH pathway in human reproductive health and disease," Human Reproduction Update, vol. 20, No. 4 pp. 485-500, 2014.
Sloan et al., "Methodologic Lessons Learned From Hot Flash Studies," J. Clin. Oncol. 19(23):4280-90 (2001).
Stratton et al., "Anxiolytic activity of tachykinin NK2 receptor antagonists in the mouse light-dark box," Eur J Pharmacol 250{3):R11-2 (1993).
Streuli, et al., "An update on the pharmacological management of adenomyosis," Expert. Opin. Pharmacolther (2014) 15(16):2347-2360.
Struthers, et al., "Suppression of gonadotropins and estradiol in premenopausal women by oral administration of the nonpeptide gonadotropin-releasing hormone antagonist elagolix", J. Clin Endocrinol Metab, Feb. 2009, 94 (2):545-551.
Tataryn Iv, et al., "LH, FSH and skin temperature during the menopausal hot flash", JCE & M 1979, vol. 49, No. 1, pp. 152-154.
Taziaux, et al., "Sex differences in the neurokinin B system in the human infundibular nucleus," J. Clin Endocrinol Metab 97:E2210-E2220, 2012.
Te Beek, et al., "Pharmacokinetics and central nervous system effects of the novel dual NK1/NK3 receptor antagonist GSK1144814 in alcohol intoxicated volunteers," Br. J Clin Pharmacol 75:5 1328-1339.
Abel, et al,, "Stereologic study of the hypothalamic infundibular nucleus in young and older women", The Journal of Comparative Neurology, 424:679-688 (2000)..
Abel, et al., "The effects of hormone replacement therapy on hypothalamic neuropeptide gene expression in a primate model of menopause," JCE & M 1999 vol. 84, No. 6, pp. 2111-2118.
Archer et al., "A double-blind, randomly assigned, placebo-controlled study of desvenlafaxine efficacy and safety for he treatment of vasomotor symptoms associated with menopause," Am J Obstet Gynecol. 200(2):172.e1-10 (2009).
Archer et al., "A randomized, double-blind, placebo-controlled study of the lowest effective dose of drospirenone with 17A-estradiol for moderate to severe vasomotor symptoms in postmeno-

(56) References Cited

OTHER PUBLICATIONS pausal women," Menopause: The Journal of The North American Menopause Society 21(3):227-235 (2014).

Arisawa, et al., "Stimulatory role of substance P on gonadotropin release in ovariectomized rats," Neuroendocrinology, 1990; 51:523-529.

Azziz, et al., "Positions statement: criteria for defining polycystic ovary syndrome as a predominantly hyperandrogenic syndrome: an Androgen Excess Society guideline," J_ Clin Endocrinol. Metab 91: 4237-4245, 2006.

Bardia, et al. "Pilot evaluation of Aprepitant for the treatment of hot flashes," Supportive Cancer Therapy, vol. 3, No. 1, 240-246, 2006.

Bertrand et al., "Capsaicin Increases Airflow Resistance in Guinea Pigs In Vivo by Activating both NK2 and NK1 Tachykinin Receptors," Am. Rev. Respir. Dis.148:909-914 (1993).

Biissantz et al., "Identification of Crucial Amino Acid in the Helix Position 6.51 of Human tachkinin Neurokininn 1 and 3 Receptor contributing to the insurmountable Mode of antagonism by dual NK1/NK3 Antagonists," J_ Med. Chem. 2012, 55, 5061-5076.

Billings, et al., "Neurokinin B acts via the neurokinin-3 receptor in the retrochiasmatic area to stimulate luteinizing hormone secretion in sheep," Endocrinology, 151:3836-3846, 2010.

Biran, et al., "Direct Regulation of Gonadotropin Release by Neurokinin B in Tilapia {Oreochromis niloticus)," Endocrinology 155:1-12, 2014.

Borsay Ba, et al., "Hypophysiotropic gonadotropin-releasing hormone projections are exposed to dense plexuses of kisspeptin, neurokinin B and substance p immunoreactive fibers in the human: a study on tissues from postmenopausal women", Neuroendocrinology 2014; 100-141-152.

Bouchard et al., "Randomized placebo- and active-controlled study of desvenlafaxine for menopausal vasomotor symptoms," Climacteric 15(1):12-20 (2012).

BRISDELLE® {paroxetine) capsules, for oral use prescription label. Revised Jan. 2017. Reference ID: 4036886.

Brown, et al., "Gonadal steroid regulation of substance P {SP) and SP-encoding messenger ribonucleic acids in the at anterior pituitary and hypothalamus," Endocrynology 126:330-340, 1990.

Brylla, et al., "Coexpression of preprotachykinin A and B transcripts in the bovine corpus luteum and evidence for Functional neurokinin receptor activity in luteal endothelial cells and ovarian macrophages," Regulatory Peptides, 125 (2005) 125-133.

Burke, et al., "Coexpression of dynorphin and neurokinin B immunoreactivity in the rat hypothalamus: Morphologic Vidence of interrelated function within the arcuate nucleus," The journal of Comparative Neurology 498:712-726 2006).

Candenas, et al., "Changes in the expression of tachykinin receptors in the rat uterus during the course of regnancy,", Biology of Reproduction, 65, 538-543 (2001).

Casper, et al., "Menopausal flushes: a neuroendocrine link with pulsatile luteninizing hormone secreation," Science, vol. 205, 1979, pp. 823-825.

Casper, et al., "Menopausal flushes: effect of pituitary gonadotropin desensitization by a potent luteinizing hormone-releasing factor agonist," JCE & M, 1981, vol. 53 No. 5, pp. 1056-1058.

Catalani, et al., "Identification of novel NK1/NK3 dual antagonists for the potential treatment of schizophrenia," Bioorganic & Medicinal Chemistry Letters, 21 (2011) 6899-6904.

Chawla, et al., "Localization of neurons expressing substance P and neurokinin B gene transcripts in the human hypothalamus and basal forebrain", The Journal of Comparative Neurology, 384:429-442 (1997).

Cheng, et al., "The kisspeplin/neurokinin B/dynorphin (KNDy) cell population of the arcuate nucleus: sex differences nd effects of prenatal testosterone in sheep," Endocrinology 151:301-311, 2010.

Ciofi, et al., "Presence of nuclear androgen receptor-like immunoreactivity in neurokinin B-conlaining neurons of the hypothalamic arcuate nucleus of the adult male rat," Neuroscience Letters 182 (1994) 193-196.

Communication pursuant to Rules 161(1) and 162 EPC pertaining to corresponding European Patent Application No. 16723107.5 dated Jan. 3, 2018.

Dacks, et al., "Activation of neurokinin 3 receptors in the median preoptic nucleus decreases core temperature in the al," Endocrinology 152:4894-4905, 2011.

Danocka et al., "Antidepressant-type effect of the NK3 tachykinin receptor agonist aminosenktide in mouse lines differing in endogenous opioid system activity," Peptides 22(7): 1037-42 (2001).

Daoui et al., "Involvement of Tachykinin NK3 Receptors in Citric Acid-induced Cough and Bronchial Response in 3uinea Pigs," Am. J_ Respir. Grit. Care Med. 158:42-48 (1998).

Datacchini et al., "Tachykinin NK1 and NK2 receptors mediate inhibitory vs excitatory motor responses in human solated corpus cavernosum and spongiosum," Br J Pharmacol. 135(6):1351-4 (2002).

Dawson, et al., "Progress in the development of neurokinin 3 modulators for the treatment of schizophrenia molecule development and clinical progress," Future Med Chem (2013) 5(13), 1525-1546.

De Croft S., et al., "Neurokinin B activates arcuate kisspeptin neurons through multiple tachykinin receptors in the male mouse", Endocrinology 154:2750-2760, 2013.

Dellovade, et al., "Estrogen regulation of neurokinin B gene expression in the mouse arcuate nucleus is mediated by estrogen receptor alpha," Endocrinology 145(2):736-742 2004.

DiMasi et al., "Trends in Risks Associated With New Drug Development: Success Rates for Investigational Drugs," Clinical Pharmacology & Therapeutics 87(3):272-277 (2010).

Ebede, et al., "Hormonal Treatment of Acne in Women," J Clin Aesthetic Denmalol. 2009;2(12):16-22.

Emend (aprepitant) capsules, for oral use prescription label. Revised: Dec. 2012. Reference ID: 3283529.

Endo, et al., "Effects of senklide, a neurokinin 3 receptor agonisl, on luleinizing honrnone secretion and follicular Tevelopmenl in anestrous Shiba goats: a pilot study," BMC Research Note 2014, 7:773.

Escobar-Morreale, et al., "Epidemiology, diagnosis and management of hirsutism: a consensus statement by the Androgen Excess and Polycystic Ovary Syndrome Society," Human Reproduction Update vol. 18, No. 2, pp. 146-170, 2012.

Fergani C, et al., "Do Substance P and Neurokinin A play important roles in the control of LH secretion in ewes?", Endocrinology 2016-1565 1-13.

Fleury, et al., "A pharmacokinetic-pharmacodynamic model for cardiovascular safety assessment," Journal of Pharmacological and Toxicological Methods 63 2011) 123-133.

Foulon et al., "Nk1 and NK2 Receptors Mediate Tachykinin and Resiniferatoxin-Induced Bronchospasm in Guinea Pigs," Am Rev Respir Dis 148:915-921 (1993).

Francou, et al., "Normosmic congenital hypogonadotropic hypogonadism due to TAC3ITACR3 mutations haracterization of neuroendocrine phenotypes and novel mutations," PLoS ONE 6(10:e25614.

Fukami, et al., "Hypothalamic dysfunction in a female with isolated hypogonadotropic hypogonadism and compound heterozygous TACR3 mutations and clinical manifestation in her heterozygous mother," Horm Res Paediatr. 2010;73:477-481.

Garcia-Galiano, et al., "Kisspeptin signaling is indispensable for neurokinin B, but not glutamate, stimulation of Gonadotropin secretion in mice," Endocrinology 153:316-328, 2012.

Garcia-Ortega J., et al., "Expression of tachykinins and tachykinin receptors and interaction with kesspeptin in human granulosa and cumulus cells", Biol Reprod Jun. 2016; 94(6) Epub May 4, 2016.

Garcia-Ortega, et al., Expression of neurokinin B/NK3, Human Reproduction, vol. 0, No. 0 pp. 1-11, 2014.

Garcia-Recio et al., "Biological and Pharmacological Aspects of the NK1-receptor," Biomed Res Int. 2015:495704 (2015).

George, et al., "The Neurokinin B Receptor Antagonist AZD4901 Decreases LH and Testosterone Secretion in Women with Pcos: A Randomised, Double-Blind, Placebo-Controlled Clinical Trial," Ptogram: Abstracts-Orals, Poster Previews, and Posters Session: OR27-Hyperandrogenic Ovarian Dysfunction Basic/Clinica, Saturday Mar. 7, 2015.

(56) References Cited

OTHER PUBLICATIONS

Gianetti, et al. "TAC3/TACR3 mutations reveal preferential activation of gonadotropin-releasing hormone release by neurokinin B in neonatal life followed by reversal in adulthood," J_ Clin. Endocrinol Metab 95; 2857-2867, 2010.

Gollnick, et al., "Management of acne: a report from a Global Alliance to Improve Outcomes in Acne," J_ Am Acad. Dermatol. vol. 49, No. 1, 2003 pp. S1-S37.

Gonzalez-Santana A, et al., "Altered expression of the tachykinins substance P/neurokinin A/hemokinin-1 and their preferred neurokinin 1/neurokinin 2 receptors in uterine leiomyomata", Reproductive Science, vol. 106, Nov. 6, 2016, 1521-1529.

Teixeira et al., "Effects of central administration of tachykinin receptor agonists and antagonists on plus-maze behavior in mice," Eur J Pharmacol. 5;311(1):7-14 (1996).

Topaloglu, et al., "TAC3 and TACR3 mutations in familial hypogonadotropic hypogonadism reveal a key role for Neurokinin B in the central control of reproduction," Nature Genetics, No. 3, Mar. 2009 354-358.

Trower MK, et al., "Evidence for rapid and sustained target engagement by a dual mechanism neurokinin-3,1 receptor antagonist on hypothalamic KNDy neurons; results from Phase 1 studies with NT-814, a potential novel therapy for sex hormone-dependent diseases", Abstract of Kisspeptin Meeting (2017).

Varothai, et al., "Androgenetic Alopecia: An Evidence-Based Treatment Update," Am J Clin Dermatol (2014) 15:217-230.

Vijayan, et al., "In Vivo and In Vitro effects of substance P and neurotensin on gonadotropin and prolactin release,", Endocrinology, 105:64, 1979.

Wakabayashi, et al., "Neurokinin B and dynorphin A in kisspeptin neurons of the arcuate nucleus participate in generation of periodic oscillation of neural activity driving pulsatile gonadotropin-releasing hormone secretion in the goat," The Journal of Neuroscience, Feb. 24, 2010, 30(8):3124-3132.

Weems PW, et al., "The Roles of Neurokinins and Endogenous Opioid Peptides in Control of Pulsatile LH Secretion", Vitamins and Hormones, vol. 107, Chapter 4, 89-135 (2018).

Yamamura T., et al., "Effects of intravenous administration of neurokinin receptor subtype-selective agonists on gonadotropin-releasing hormone pulse generator activity and luteinizing hormone secretion in goats", J. Reprod. Dev. 61:20-29, 2015.

Yamamura, et al., "Effects of intravenous administration of neurokinin receptor subtype-selective agonists on gonadotropin-releasing hormone pulse generator activity and luteinizing hormone secretion in goats," J. Reprod. Dev. 61:20-29,2015.

Yang, et al., "Uncovering novel reproductive defects in neurokinin B receptor null mice: closing the gap between mice and men," Endocrinology 153:1498-1508, 2012.

Young, et al., "TAC3 and TACR3 defects cause hypothalamic congenital hypogonadotropic hypogonadism in humans," J Clin Endocrinol. Metab, May 2010 95(5):2287-2295.

Guran, et al., "Hypogonadotropic hypogonadism due to a novel missense mutation in the first extracellular loop of the neurokinin B receptor," J Clin Endocrin Metab 94:3633-3639, 2009.

Hanessian, et al., "Design and synthesis of potential dual NK1/NK3 receptor antagonists," Bioorg. Med. Chem. Lett 24 (2014) 510-514..

Hanessian, et al., "Design, Synthesis, and Optimization of Balanced Dual NK1/NK3 Receptor Antagonists," ACS Med. Chem. Lett. 2014, 5, 550-555.

Hofmann, et al., "Discovery of potent, balanced and orally active dual NK1/NK3 receptor ligands", Bioorganic & Medicinal Chemistry Letters 20 (2010) 3405-3408.

Hoveyda, et al., "Discovery and optimization of novel antagonists to the human neurokinin-3 receptor for the treatmenl of sex-hormone disorders (Part I)," J_ Med. Chem. 2015, 58, 3060-3082.

Hrabovszky, et al., "Low degree of overlap between kisspeplin, neurokinin B, and dynorphin immunoreactivities in the infundibular nucleus of young male human subjects challenges the KNDy neuron concept," Endocrinology 153:4978-4989, 2012.

Hrabovszky, et al., "The kisspeplin system of the human hypothalamus: sexual dimorphism and relationship with gonadotropin-releasing hormone and neurokinin B neurons," European Journal of Neuroscience, vol. 31, pp. 1984-1998, 2010.

Hrabovxzky E., et al., "Substance P immunoreactivity exhibits frequent colocalization with kisspeptin and neurokinin B in the human infundibular region", PLOS ONE , Aug. 2013, vol. 8, issue 8 e72369 1-11.

International Patent Application No. PCT/EP2016/060945. Search Report and Written Opinion (ISR).

Jayasena, et al., "Neurokinin B Administration Induces Hot Flushes in Women," Sci. Rep. 5, 8466: 1-7 (2015).

Kalil, B., et al.,"The Distribution of Substance P and Kisspeptin in the Mediobasal Hypothalamus of the Male Rhesus Monkey and a Comparison of Intravenous Administration of These Peptides to Release GnRH as Reflected by LH Secretion", Neuroendocrinology. 2016: 103(6): 711-723.

Karagiannides, et al., "Substance P (SP)-Neurokinin-l Receptor (NK-1R) Allers Adipose Tissue Responses to High-Fat Diel and Insulin Action," Endocrinology 152:2197-2205, 2011.

Karsch, F.J., "Central actions of ovarian steroids in the feedback regulation of pulsalile secretion of luteinizing hormone," Ann. Rev. Physiol., 1987, 49:365-82.

Kinsey-Jones, et al., "The inhibitory effects of neurokinin B on GnRH pulse generator frequency in the female rat," Endocrinology 153:307-315, 2012.

Krajewski, et al., "Forebrain projections of arcuate neurokinin B neurons demonstrated by anlerograde tract-tracing and monosodium glutamate lesions in the rat," Neuroscience Mar. 17, 2010; 166(2):680-697.

Krajewski, et al., "Morphologic evidence that neurokinin B modulates gonadotropin-releasing hormone secretion via neurokinin 3 receptors in the rat median eminence," The Journal of Comparative Neurology, 489:372-386 (2005).

Larsen, P. J., "Distribution of substance P-immunoreactive elements in the preoptic area and the hypothalamus of the rat," The Journal of Comparative Neurology, 316:287-313 (1992).

Lasaga M., et al., "Tachykinins and the hypothalamo-pituitary-gonadal axis: An update", Peptides 32 (2011) 1972-1978.

Lasaga, et al., "Tachykinins and the hypothalamo-pituitary-gonadal axis_An update," Peptides 32 (2011) 1972-1978.

Lee, et al., "Influence of substance-P on cultured sebocytes," Arch Dermatol Res (2008) 300:311-316.

Lehman, et al., "Minireview: kisspeptin/neurokinin B/dynorphin (KNDy) cells of the arcuate nucleus: a central node in the control of gonadotropin-releasing hormone secretion," Endocrinology 151:3479-3489, 2010).

Li, et al., "Evidence that Neurokinin B Controls Basal Gonadotropin-Releasing Hormone Secretion but Is Not Critical tor Estrogen-Positive Feedback in Sheep," Neuroendocrinology 2015; 101:161-174.

Litman, et al., "The Selective Neurokinin 3 Antagonist AZD2624 Does Not Improve Symptoms or Cognition in Schizophrenia," J Clin Psychopharmacol 2014;34: 199-204.

Louis et al., "Additional evidence for anxiolytic- and antidepressant-like activities of saredutant {SR48968), an antagonist at the neurokinin-2 receptor in various rodent-models," Pharmacol Biochem Behav. 89(1):36-45 (2008).

Lucky, et al., "Plasma Androgens in Women with Acne Vulgaris," Journal of Investigative Dermatology, 81:70-74, 1983.

Maclennan et al., "Oral oestrogen and combined oestrogen/progestogen therapy versus placebo for hot flushes," Cochrane Database Syst Rev. 18;(4):CD002978 (2004).

Maguire, et al., "The Role of Substance P in the Central Control of Food Intake," Program: Abstracts-Orals, Posters Previews, and Poster Session, Energy Balance: Control of Adiposity and Feeding Basic. Saturday Mar. 7, 2015.

Malherbe, et al., "Characterization of RO4583298 as a novel potent, dual antagonist with in vivo activity at tachykinin NK1 and NK3 receptors," British Journal of Pharmacology, (2011) 162 929-946.

Malherbe, et al., "Tachykinin neurokinin 3 receptor antagonists: a patent review (2005-2010)," Expert. Opin. Ther. Patents (2011) 21(5):637-655.

(56) References Cited

OTHER PUBLICATIONS

McKinnon, et al., "Induction of the neurokinin 1 receptor by TNFα in endometriotic tissue provides the potential for neurogenic control over endometriotic lesion growth," J Clin Endocrinol Metab 98:2469-2477, 2013.

Merkley, et al., "KNDy (kisspeptin/neurokinin B/dynorphin) neurons are activated during both pulsatile and surge secretion of LH in the ewe," Endocrinology 153:5406-5414, 2012.

Millar, et al., "Current and future applications of GnRH, kisspeptin and neurokinin B analogues," Nat. Rev. Endocrinol. 9, 451-466(2013).

Mittelman-Smith, et al., "Role for kisspeptin/neurokinin B/dynorphin (KNDy) neurons in cutaneous vasodilatation and the estrogen modulation of body temperature," PNAS Nov. 27, 2012 vol. 109, No. 48 19846-19851.

Mittelman-Smith, et al. "Neurokinin 3 Receptor-Expressing Neurons in the Median Preoptic Nucleus Modulate Heat-Dissipation Effectors in the Female Rat," Endocrinology 156:2552-2562, 2015.

Mittelman-Smith, et al., "Arcuate kisspeptin/neurokinin B/dynorphin (KNDy) neurons mediate the estrogen suppression of gonadotropin secretion and body weight," Endocrinology 153:2800-2812, 2012.

Molnar, et al., "Morphological Evidence for Enhanced Kisspeptin and Neurokinin B Signaling in the Infundibular Nucleus of the Aging Man," Endocrinology 153:5428-5439, 2012.

Navarro VM, et al., "The integrated hypothalamic tachykinin-kisspeptin system as a central coordinator for reproduction", Endocrinology 156: 627-637, 2015.

Navarro, et al.,"Role of neurokinin B in the control of female puberty and its modulation by metabolic status," The Journal of Neuroscience, Feb. 15, 2012 32(7):2388-2397.

Navarro, et al., "Interactions between kisspeptin and neurokinin B in the control of GnRH secretion in the female rat," Am J. Physiol Endocrinol Metab 300:E202-E210, 2011.

Navarro, et al., "Regulation of gonadotropin-releasing hormone secretion by kisspeptin/dynorphin/neurokinin B neurons in the arcuate nucleus of the mouse," J Neurosci. Sep. 23, 2009; 29(38):11859-11866.

Navarro, et al., "Regulation of NKB pathways and their roles in the control of Kiss 1 Neurons in the arcuate nucleus of the male mouse," Endocrinology 152:4265-4275, 2011.

Navarro, et al., "The integrated hypothalamic tachykinin-kisspeptin system as a central coordinator for reproduction," Endocrinology 156:627-637, 2015.

Nestor, et al., "Evidence of a role for kisspeptin and neurokinin B in puberty of female sheep," Endocrinology, 153:2756-2765, 2012.

Ng, "Chapter 5: Drug Development and Preclinical Studies," Drugs From Discovery to Approval, Second Edition, John Miley & Sons, Inc., pp. 136-175 (2009).

Ng, "Chapter 6: Clinical Trials," Drugs From Discovery to Approval, Second Edition, John Wiley & Sons, Inc., pp. 176-207 (2009).

Noritake K, et al., "Involvement of neurokinin receptors in the control of pulsatile luteinizing hormone secretion in rats", J. Reprod. Dev. 57:409-415, 2011.

Okamura H, et al., "Mapping of KNDy neurons analysis of the interaction between KNDy and SP neural systems in goat", J Reprod. Dev. 63:571-580, 2017.

Overgaard, et al., "Disparate changes in kisspeptin and neurokinin B expression in the arcuate nucleus after sex steroid manipulation reveal differential regulation of the two KNDy peptides in rats," Endocrinology 155:3945-3955, 2014.

\* cited by examiner
‡ imported from a related application

METHOD OF TREATMENT OF SYMPTOMS OF MENOPAUSE

This Non-Provisional Application is a divisional application of U.S. patent application Ser. No. 16/351,659, filed Mar. 13, 2019, which claims priority to and the benefit of U.S. Provisional Application No. 62/642,622 filed on Mar. 14, 2018 the contents of which are incorporated herein by reference in their entireties.

FIELD OF THE INVENTION

This invention relates to novel pharmaceutical formulations containing dual NK-1/NK-3 receptor antagonists, specifically including 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide, methods of preparation thereof and their use in medical therapy.

BACKGROUND OF THE INVENTION

Tachykinins belong to a family of short peptides that are widely distributed in the mammalian central and peripheral nervous system (Bertrand and Geppetti, Trends Pharmacol. Sci. 17: 255-259 (1996)). They share the common C-terminal sequence Phe-Xaa-Gly-Leu-Met-NH2. The three major tachykinins are Substance P (SP), Neurokinin A (NKA) and Neurokinin B (NKB) with preferential affinity for respectively three distinct receptor subtypes, termed Neurokinin (NK)-1, NK-2, and NK-3.

Compounds showing selective affinity simultaneously to both NK-1 and NK-3 receptors are named dual NK-1/NK-3 receptor antagonists. For example, 2-[3,5-Bis(trifluoromethyl)phenyl]-N-{4-(4-fluoro-2-methylphenyl)-6-[(7S,9a5)-7-(hydroxymethyl)hexahydropyrazino[2,1-c][1,4]oxazin-8(1H)-yl]-3-pyridinyl}-N,2-dimethylpropanamide (Compound A), having the following structure:

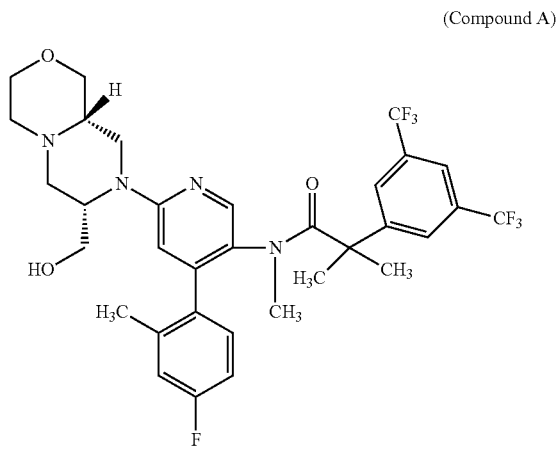 [SMILES: Cc1cc(F)ccc1-c1cc(N2C[C@H]3COCCN3C[C@H]2CO)ncc1N(C)C(=O)C(C)(C)c1cc(C(F)(F)F)cc(C(F)(F)F)c1]

(Compound A)

has been found to be effective as a dual NK-1/NK-3 receptor antagonist.

Compound A is also known in an anhydrous crystalline form. Thus Compound A in an anhydrous crystalline form is described in WO2011023733, e.g., having 2 theta angles occurring at 4.3±0.1, 7.9±0.1, 9.8±0.1, 10.7±0.1, 10.8±0.1, 13.3±0.1, 14.0±0.1, 15.1±0.1 degrees, which correspond respectively to d-spacing at 20.4, 11.1, 9.0, 8.3, 8.2, 6.6, 6.3 and 5.9 Angstroms (Å) (hereinafter "Form 1").

Compound A or pharmaceutically acceptable salts thereof, including its crystalline Form 1, are known, inter alia to be useful in the treatment of sex hormone diseases, including hot flushes (WO 2016/184829).

It is essential that, when being administered to a subject in need thereof, Compound A reaches the site of action at an amount and for a duration, as defined by the pharmacokinetic (PK) exposure, that is sufficient for a therapeutic effect to occur, while the exposure level of Compound A is not too high that it might result in treatment induced adverse reactions. Therefore there are two key parameters relating to the PK of Compound A to ensure that a dose of this drug administered to a patient consistently reaches levels of exposure so that it produces the desired therapeutic effect while minimising the potential for adverse effects. First is the PK variability which is a measure of the variation in exposures achieved with the same dose of a drug. The PK variability which is typically measured as the Coefficient of Variation as a percent (CV %) should be low such that when any given dose of a drug is administered the plasma levels (both maximum plasma concentration that a drug achieves [Cmax] and exposure [Area under the Curve [AUC]] in subjects are similar. Certainly the CV % achieved for these measures with any given dose of a particular drug should be typically <50%. Second is the bioavailability of Compound A, which defines the proportion of a drug from an administered dosage form that reaches the systemic circulation and therefore dictates the level of drug exposure. The bioavailability achieved with a dose of a particular drug when administered to a subject needs to be able to reach the desired therapeutics levels of exposure.

It is known that the formulation of a drug (dosage form) namely the process by which the active drug is combined with other different inactive chemical substances (excipients), to produce a final drug product can influence these two critical PK parameters. However such formulations also need to maintain the stability of the active drug ideally at ambient conditions for long term storage. Maintenance of stability of the active drug is therefore the third key parameter required for development of a novel drug product formulation.

Previously, Compound A as Form 1, was formulated for oral administration as solid dosage forms of drug product and these were administered to human subjects in both Phase 1 and 1b/2 clinical studies.

The PK data from a tablet solid dose formulation administered as single oral doses of either 100 mg or 200 mg of Compound A (Form 1) to 16 healthy male and female volunteers in a Phase 1 study is summarized in Table 1. The results revealed an unacceptable level of PK variability as measured by CV % that ranged from 69.9% to 120%, and high Ratios of Minimum & Maximum PK parameters ranging from 9.8 to 20.1.

TABLE 1

PK data from a single dose Phase 1 clinical study with Compound A(Form1)
using a solid dose tablet drug product
Development Form: Anhydrous crystalline form (Form1)
Study populations: Male and Female Healthy Volunteers

| Formulation | PK parameter | Dose (mg) | N | Geometric Mean | CV % | Minimum (Min) | Maximum (Max) | Ratio (Max:Min) |
|---|---|---|---|---|---|---|---|---|
| Solid | Cmax | 100 | 16 | 880 | 101 | 120 | 2411 | 20.1 |
| tablet^ | (ng/mL) | 200 |  | 795 | 120 | 169 | 2268 | 13.4 |
| doses | $AUC_{0\text{-}24}$ | 100 |  | 3309 | 69.9 | 679 | 6625 | 9.8 |
| (single dose) | (ng · hr/mL) | 200 |  | 4424 | 76.3 | 1237 | 12937 | 10.5 |

Key:
CV % = Coefficient of variation percent
^Powder blend of Compound A anhydrous crystalline form (Form1) which has been compressed to obtain a tablet drug product A second Phase 1b/2 clinical study was undertaken involving repeated dosing of an additional solid dose hard gelatin capsule formulation of Compound A (Form 1) in post-menopausal women experiencing moderate to severe vasomotor symptoms. The doses investigated were 50, 100, 150 and 300 mg, orally administered once daily for 14 days. There were 13 or 15 subjects per dose group. All doses were given using the 50 mg capsule formulation. To achieve unit doses higher than 50 mg, appropriate multiples of capsules were concomitantly administered to patients in each of the dose groups. Steady-state PK results after 14 days dosing are presented in Table 2. Once more an unacceptably high level of PK variability was observed in this repeat dose study with the hard capsule solid dosage drug product as measured by CV % that ranged from 64.7% to 131.2%, and high Ratios of Minimum & Maximum PK parameters ranging from 6.1 to 36.5.

The efficacy assessments demonstrated that 'maximum efficacy' in this Phase 1b/2 study was achieved with a once daily dose hard gelatin drug product of 150 mg Compound A (requiring three 50 mg hard gelatin capsules). Repeat once-a-day dosing of 150 mg Compound A gave a geometric mean exposure $AUC_{0\text{-}24}$ 5164 ng·hr/mL of the drug at Day 14.

TABLE 3

Composition of solid dose hard gelatin capsule formulation
containing 50 mg of Compound A[Form 1] administered
in the Phase 1b/2 study.

| Ingredients | Quantity per Capsule (mg) | Functionality |
|---|---|---|
| Compound A (Form1) | 50.00 | Active |
| Intra-granular Ingredients |  |  |
| Lactose Monohydrate (Spray Dried) | 47.10 | Filler Agent |
| Microcrystalline Cellulose, (Avicel PH-101) | 33.04 | Filler Agent |

TABLE 2

Steady-state PK data from a repeat dose Phase 1b/2 clinical study with
Compound A(Form1) using a solid dose hard gelatin drug product
Development Form: Anhydrous crystalline form (Form1)
Study populations: Post-menopausal females experiencing moderate to severe vasomotor symptoms

| Formulation | PK parameter | Dose (mg) | N | Geometric Mean | CV % | Minimum (Min) | Maximum (Max) | Ratio (Max:Min) |
|---|---|---|---|---|---|---|---|---|
| Solid hard | Cmax | 50 | 15 | 522 | 87.9 | 142 | 1544 | 10.9 |
| gelatin | (ng/mL) | 100 | 14 | 841 | 107.2 | 181 | 3856 | 21.3 |
| capsule |  | 150 | 15 | 1188 | 131.2 | 208 | 5903 | 28.4 |
| doses |  | 300 | 13 | 2852 | 116.5 | 237 | 8653 | 36.5 |
| (Steady-state | $AUC_{0\text{-}24}$ | 50 | 15 | 2342 | 64.7 | 915 | 5540 | 6.1 |
| Day 14) | (ng · hr/mL) | 100 | 14 | 3542 | 86.3 | 778 | 10938 | 14.1 |
|  |  | 150 | 15 | 5164 | 88.7 | 1564 | 16163 | 10.3 |
|  |  | 300 | 13 | 14823 | 99.7 | 2457 | 79685 | 32.4 |

Key:
CV % = Coefficient of variation percent
^ Powder blend of Compound A anhydrous crystalline form (Form1) which has been encapsulated in a hard gelatin capsule. The specific composition of a solid dosage hard gelatin capsule formulation containing 50 mg of Compound A is provided in Table 3.

TABLE 3-continued

Composition of solid dose hard gelatin capsule formulation containing 50 mg of Compound A[Form 1] administered in the Phase 1b/2 study.

| Ingredients | Quantity per Capsule (mg) | Functionality |
|---|---|---|
| Hypromellose 2910 | 5.55 | Binder |
| Croscarmellose Sodium | 1.67 | Disintegrant |
| Purified Water (removed during processing) | 22.22 | Granulating Solution |
| Extra-granular ingredients | | |
| Lactose Anhydrous (Super Tab 21AN) | 21.89 | Filler Agent |
| Microcrystalline Cellulose (PH-102) | 35.00 | Filler Agent |
| Croscarmellose Sodium | 5.25 | Disintegrant |
| Magnesium Stearate | 1.75 | Lubricating Agent |
| Total (intra- and extra-granular) | 201.25 | |
| Empty Hard Gelatin Capsule, Size 2, Opaque White/White | 1 unit | Capsule Shell |

Despite levels of drug exposure being achieved that were efficacious in the Phase 1b/2 clinical study, neither of these solid dose formulations of Compound A are suitable for further clinical development due to the very high PK variability observed in these human subjects.

Therefore, there is a need for a novel pharmaceutical formulation of Compound A or a pharmaceutically acceptable salt thereof that provides a reduced human subject PK variability, thereby reducing the likelihood of very high drug exposures being reached in individual patients and ensuring a much safer medicine; as well as avoiding too low exposures which would mean patients do not receive a therapeutically beneficial dose of Compound A. Such formulations must also have sufficient bioavailablity to be able to achieve therapeutic levels of plasma exposure of Compound A. In addition such formulations must provide good stability of Compound A during manufacture and subsequent distribution and long term storage of the drug product.

A soft gelatin capsule formulation could provide an approach to address these needs. However, it is known to those in the art, that formulating drugs into solution for encapsulation into a soft gelatin capsule can be challenging and can present many problems (Gullapalli, 2010). These challenges include the migration of the soft gelatin constituents between the formulation, the shell and external environments; nor must there be physical and chemical incompatibilities between the components. In addition, it can be difficult to identify liquid matrices in which an active ingredient is sufficiently soluble to dissolve the desired target dose in a suitably small volume to be encapsulated for oral administration; that does not precipitate out during the manufacturing process, upon storage for the duration of the required shelf-life, upon contract with the aqueous environment (dissolution) nor once administered in vivo. Also, it can be problematic to identify formulations in which drug substances are stable for long term storage encapsulated in the soft gelatin capsules as they are susceptible to both hydrolytic and oxidative instability.

These technical challenges have been unexpectedly overcome and the formulations according to the present invention address all the three key parameters described above.

Particularly, the present disclosure is based on, inter alia, our unexpected discovery of novel formulations of Compound A that provide remarkably reduced PK variability of Compound A and that can achieve therapeutic levels of plasma exposure. Furthermore, it was discovered that such formulations effectively solubilize Compound A in a volume suitable for oral administration and exhibit long-term storage stability at ambient conditions without recrystallization, precipitation, or phase separation.

SUMMARY OF THE INVENTION

The present invention provides, inter alia, a pharmaceutical formulation, comprising:

(a) 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide (Compound A):

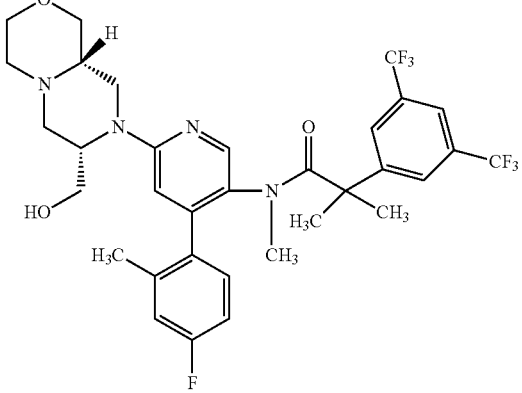

(Compound A)

or a pharmaceutically acceptable salt thereof;

(b) at least one solubilizer

In some aspects, the present invention provides a pharmaceutical formulation, comprising:

(a) Compound A; and (b) at least a solubilizer

In some embodiments, Compound A is in a crystalline form. In some embodiments, Compound A is in anhydrous crystalline Form 1. In some embodiments, the pharmaceutical formulation further comprises an antioxidant. In some embodiments, the pharmaceutical formulation further comprises an emulsifier.

In some embodiments, the pharmaceutical formulation further comprises one or more additional therapeutic agents. In some embodiments, the pharmaceutical formulation is an oral formulation. In some embodiments, the pharmaceutical formulation is a liquid oral formulation.

In some aspects, the present invention provides a pharmaceutical kit, consisting a first package comprising the pharmaceutical formulation of any one of the preceding claims, and a second package comprising one or more additional therapeutic agents.

In some aspects, the present invention provides a method of treating or preventing a disease or a condition disclosed herein, comprising administering to a subject in need thereof a pharmaceutically effective amount of Compound A.

In some aspects, the present invention provides a pharmaceutical formulation disclosed herein for use in the treatment or prevention of a disease or a condition disclosed herein.

In some aspects, the present invention provides a pharmaceutical formulation disclosed herein for use in combination with one or more additional therapeutic agents in the treatment or prevention of a disease or a condition disclosed herein.

In some aspects, the present invention provides a combination of a pharmaceutical formulation disclosed herein and one or more additional therapeutic agents for use in the treatment or prevention of a disease or a condition disclosed herein.

In some aspects, the present invention provides use of a pharmaceutical formulation disclosed herein in the manufacture of a medicatment for treating or preventing a disease or a condition disclosed herein.

In some aspects, the present invention provides use of a pharmaceutical formulation disclosed herein in combination with one or more additional therapeutic agents in the manufacture of a medicatment for treating or preventing a disease or a condition disclosed herein.

In some aspects, the present invention provides use of the combination of a pharmaceutical formulation disclosed herein and one or more additional therapeutic agents in the manufacture of a medicatment for treating or preventing a disease or a condition disclosed herein.

In some embodiments, the disease is a sex-hormone dependent disease. In some embodiments, the disease is hot flushes. In some embodiments, the disease is a weight-related disease. In some embodiments, the disease is a leptin-related disease. In some embodiments, the disease is a disorder of pregnancy. In some embodiments, the condition is one or more symptoms of the perimenopause, the menopause, or the post-menopause. In some embodiments, the condition is pathological gain of excess body fat and/or excess body weight, diabetes, hot flushes, night sweats, night-time awakening. In some embodiments, the condition is one or more symptoms of the andropause.

In a further aspect, the invention provides a method for preparing formulations according to the invention by mixing the active ingredient with at least one excipient.

It is a further aspect of the invention to provide a method for producing a soft gelatin capsule comprising the steps of providing a soft gelatin capsule shell, mixing a formulation comprising Compound A or pharmaceutically acceptable salts thereof and at least one excipient, and encapsulating the liquid formulation into the soft gelatin capsule shell.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

In the case of conflict between the chemical structures and names of the compounds disclosed herein, the chemical structures will control.

Other features and advantages of the disclosure will be apparent from the following detailed description and claims.

DETAILED DESCRIPTION OF THE INVENTION

Definitions

Figure 1:
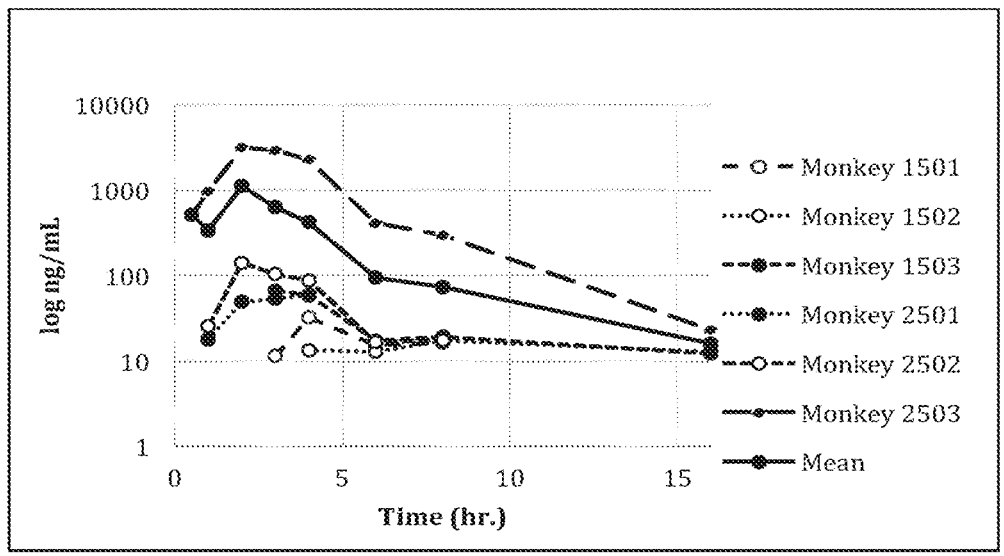
FIG. 1 provides PK plots for individual animals and means for the hard gelatin solid dose formulation of Compound A.

All numbers expressing quantities, percentages or proportions, and other numerical values used in the specification and claims, are to be understood as being modified in all instances by the term "about."

The terms "a" and "an" as used herein refer to "one or more" of the enumerated components. It will be clear to one of ordinary skill in the art that the use of the singular includes the plural unless specifically stated otherwise.

The term "sex hormone-dependent disease" as used herein refers to a disease which is exacerbated by, or caused by, excessive, inappropriate including lack of, imbalanced, or unregulated sex hormone production. Examples of such disease in men include, but are not limited to, benign prostatic hyperplasia (BPH), metastatic prostatic carcinoma, testicular cancer, breast cancer, androgen dependent acne, seborrhoea, hypertrichosis, male pattern baldness and in boys precocious puberty. Examples of such disease in women include, but are not limited to, endometriosis, abnormal puberty, uterine fibrosis, uterine fibroid tumor, heavy menstrual bleeding, dysfunctional uterine bleeding, hormone-dependent cancers (breast, endometrial, ovarian, uterine), hyperandrogenism, hirsutism, hypertrichosis, female androgenetic alopecia, androgen dependent acne, seborrhoea, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility) and androgen-producing tumor (virilizing ovarian or adrenal tumor), and osteoporosis. In men and women other examples are hidradenitis suppurativa and hot flushes.

The term "weight-related disease" as used herein refers to a disease in which the patient suffers from a pathological excess of body fat and/or excess body weight Examples of such disease include, but are not limited to, genetic susceptibility to excess body weight, obesity associated with metabolic disorders, or a condition for which a decreased body weight would be of therapeutic benefit.

The term "leptin-related disease" as used herein refers to a disease in which the leptin levels are inappropriate, including lack of, low-levels, imbalanced, or unregulated. Examples of such disease are metabolic disorders such as diabetes, cardiovascular disease, obesity, excessive eating, hypertension, metabolic syndrome and inflammatory disorders.

The term "disorder of pregnancy" as used herein means a disorder experienced by a pregnant women. Examples of such disorder are eclampsia, pre-eclampsia, gestational diabetes mellitus, high blood pressure, morning sickness, hyperemesis gravidarum, miscarriage, pelvic girdle pain, and premature birth.

The term "symptom of the menopause" as used herein means a symptom associated with the menopause which can have natural, surgical (such as bilateral oophorectomy), radiological (ie radiation therapy) or chemical causes.

Examples of such symptoms include, but are not limited to, pathological gain of excess body fat and/or excess body weight, diabetes, fatigue, irritability, cognitive decline, hair-loss, dry skin, insomnia, sleep disturbances and night-time awakenings, anxiety and depression, decreases in sexual desire, vaginal dryness and pain, connective tissue loss and muscle bulk reduction, bone loss, urinary symptoms of urgency and dysuria, hot flushes, and night sweats. In some embodiments, a symptom of the menopause in women may be caused by certain types of chemotherapy, e.g., aromatase inhibitors such as anastrozole, exemestane, letrozole and testolactone; gonadotropin-releasing hormone receptor agonists such as such as leuprolide, buserelin, histrelin, goserelin, deslorelin, nafarelin and triptorelin; gonadotropin-releasing hormone receptor antagonists such as ASP1701, elagolix, relugolix and linzagolix (OBE2109); selective estrogen receptor modulators (SERMs) such as bazedoxifene, clomifene, cyclofenil, tamoxifen, ormeloxifene, toremifene, raloxifene, lasofoxifene and ospemifene; selective estrogen receptor degraders (SERDs) such as fulvestrant, brilanestrant and elacestrant; CYP17A1 inhibitors such as abiraterone, ketoconazole and seviteronel; and combined androgen receptor blockers and CYP17A1 inhibitors such as galeterone.

The term "symptom of the perimenopause" as used herein means a symptom associated with the perimenopause which can have natural, surgical (such as bilateral oophorectomy), radiological (ie radiation therapy) or chemical causes.

The term "symptom of the post-menopause" as used herein means a symptom associated with the post-menopause which can have natural, surgical (such as bilateral oophorectomy), radiological (ie radiation therapy) or chemical causes.

The term "symptom of the andropause" as used herein refers to a symptom associated with the andropause that arises from a gradual decline in testosterone levels over the years; and may also occur also due to orchiectomy or treatment for prostate cancer called androgen deprivation therapy. Examples of such symptom are pathological gain of excess body fat and/or excess body weight, diabetes, fatigue, irritability, cognitive decline, hair-loss, dry skin, insomnia, sleep disturbances, night-time awakenings, anxiety and depression, decreases in sexual desire, connective tissue loss and muscle bulk reduction, urinary symptoms of urgency and dysuria, hot flushes and night sweats. Examples of androgen deprivation therapy that cause a symptom of the andropause in men are gonadotropin-releasing hormone receptor agonists such as such as leuprolide, buserelin, histrelin, goserelin, deslorelin, nafarelin and triptorelin; gonadotropin-releasing hormone receptor antagonists such as ASP1701, elagolix, relugolix and linzagolix (OBE2109); antiandrogens (androgen receptor blockers) such as cyproterone acetate, apalutamide, bicalutamide, darolutamide, enzalutamide, flutamide, nilutamide; CYP17A1 inhibitors such as abiraterone, ketoconazole and seviteronel; and combined androgen receptor blockers and CYP17A1 inhibitors such as galeterone.

The terms "disease", "disorder", "condition", and "symptom", as used herein, may be interchangeable and intended to have the same meaning.

The term "hot flushes" and "hot flashes", and "vasomotor symptoms" as used herein, may be interchangeable and intended to have the same meaning.

The terms "treatment," "treating,", "prevention", and "preventing", as used herein, refer to obtaining a desired pharmacologic, physiologic, dermatologic or cosmetic effect in the subject in need thereof. The effect may be prophylactic in terms of completely or partially preventing a condition or disease or disorder or symptom thereof and/or may be therapeutic in terms of a partial or complete cure for a condition or disease or disorder and/or adverse symptom or effect attributable to the condition or disease or disorder. For example, these terms may refer to any treatment or prevention of a condition or disease in a subject in need thereof (e.g., a mammal, such as a human), and include: (a) preventing the condition or disease, disorder or symptom thereof from occurring in a subject which may be predisposed to the condition or disease or disorder but has not yet been diagnosed as having it; (b) inhibiting the condition or disease, disorder or symptom thereof, such as, arresting its development; and (c) relieving, alleviating or ameliorating the condition or disease or disorder or symptom thereof, such as, for example, causing regression of the condition or disease or disorder or symptom thereof.

The term "effective amount" as used herein means that amount of a drug or a therapeutic agent or a pharmaceutical agent that will elicit the biological or medical response of a tissue, system, animal or human that is being sought, for instance, by a researcher, clinician or veterinarian.

The term "pharmaceutically acceptable salts" as used herein means salts suitable for medical applications having a pharmaceutically acceptable anion or cation.

The terms "effective amount" or "sufficient amount", as used herein, refer to an active agent, refers to the amount necessary to elicit the desired biological response. As used herein, a "pharmaceutically effective amount" or a "pharmaceutically effective dose" refers to an amount or quantity of an agent, compound, material, or composition containing a compound that is at least sufficient to produce a detectable therapeutic effect. The effect can be detected by any assay method known in the art. The precise effective amount for a subject will depend upon the subject's body weight, size, and health; the nature and extent of the condition; and the therapeutic selected for administration.

The term "subject" as used herein includes a mammal. The mammal can be e.g., any mammal, e.g., a human, primate, bird, mouse, rat, fowl, dog, cat, cow, horse, goat, camel, sheep or a pig. In some embodiments, the mammal is a human.

The term "temporal proximity" as used herein refers to that administration of one therapeutic agent (e.g., Compound A or a pharmaceutical formulation disclosed herein) occurs within a time period before or after the administration of another therapeutic agent (e.g., the one or more additional therapeutic agents), such that the therapeutic effect of the one therapeutic agent overlaps with the therapeutic effect of another therapeutic agent. In some embodiments, the therapeutic effect of the one therapeutic agent completely overlaps with the therapeutic effect of another therapeutic agent. In some embodiments, "temporal proximity" means that administration of one therapeutic agent occurs within a time period before or after the administration of another therapeutic agent, such that there is a synergistic effect between the one therapeutic agent and the other therapeutic agent "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

The term "kit" as used herein refers to a combination of components, such as a combination of the compositions herein and another item for a purpose including, but not limited to, reconstitution, activation and instruments/devices for delivery, administration, diagnosis and assessment of a biological activity or property. Kits optionally include instructions of use.

The term "excipient" as used herein refers to a solubilizer, an antioxidant or an emulsifier.

Pharmaceutical Formulations

In some embodiments, the pharmaceutical formulation of the present disclosure comprises Compound A or a pharmaceutically acceptable salt thereof.

In some embodiments, the weight of the pharmaceutical formulation ranges from about 10 mg to about 10 g, from about 20 mg to about 5 g, from about 50 mg to about 2 g, from about 100 mg to about 1 g, from about 200 mg to about 800 mg, from about 300 mg to about 700 mg, from about 350 mg to about 650 mg, from about 400 mg to about 600 mg, from about 450 mg to about 550 mg, from about 460 mg to about 540 mg, from about 470 mg to about 530 mg, from about 480 mg to about 520 mg, or from about 490 mg to about 510 mg. In some embodiments, the weight of the pharmaceutical formulation is about 500 mg.

According to some embodiments the weight of the pharmaceutical composition ranges from 500 mg to 1600 mg; particularly from 800 mg to 1200 mg.

In some embodiments, the concentration of Compound A or the pharmaceutically acceptable salt thereof in the pharmaceutical formulation ranges from about 0.1% w/w to about 50% w/w, from about 0.2% w/w to about 40% w/w, from about 0.3% w/w to about 30% w/w, from about 0.5% w/w to about 20% w/w, from about 0.8% w/w to about 15% w/w, or from about 1% w/w to about 10% w/w. Particularly, from 5% w/w to 10% w/w.

In some embodiments, the amount of Compound A or the pharmaceutically acceptable salt thereof in the pharmaceutical formulation ranges from about 1 mg to about 500 mg, from about 1 mg to about 250 mg, from about 1 mg to about 100 mg, from about 2 mg to about 50 mg, from about 3 mg to about 40 mg, from about 4 mg to about 30 mg, or from about 5 mg to about 29 mg.

In some embodiments, the amount of Compound A or the pharmaceutically acceptable salt thereof in the pharmaceutical formulation is about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, or about 29 mg.

In some embodiments, the pharmaceutical formulation of the present disclosure comprises Compound A.

In some embodiments, the concentration of Compound A in the pharmaceutical formulation ranges from about 0.1% w/w to about 50% w/w, from about 0.2% w/w to about 40% w/w, from about 0.3% w/w to about 30% w/w, from about 0.5% w/w to about 20% w/w, from about 0.8% w/w to about 15% w/w, or from about 1% w/w to about 10% w/w.

In some embodiments, the amount of Compound A in the pharmaceutical formulation ranges from about 1 mg to about 500 mg, from about 1 mg to about 250 mg, from about 1 mg to about 100 mg, from about 2 mg to about 50 mg, from about 3 mg to about 40 mg, from about 4 mg to about 30 mg, or from about 5 mg to about 29 mg.

In some embodiments, the amount of Compound A in the pharmaceutical formulation is about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, or about 29 mg.

In some embodiments, the amount of Compound A in the pharmaceutical formulation ranges from 10 mg to 80 mg. Particularly, 10 mg, 25 mg, 40 mg or 60 mg.

In some embodiments the daily dosage of Compound A in the pharmaceutical formulation ranges from 25 mg to 160 mg/day. Particularly, 25 mg, 40 mg, 60 mg, 80 mg, 100 mg, 120 mg and 160 mg/day.

Examples of Compound A and pharmaceutical salts thereof include, but are not limited to, those described in WO/2007/028654, U.S. Pat. No. 8,093,242, and WO/2011/023733, the entireties of which are incorporated herein by reference.

In some embodiments, Compound A is in a crystalline form. In some embodiments, Compound A is in a crystalline form as described in WO2011023733, e.g., having 2 theta angles occurring at 4.3±0.1, 7.9±0.1, 9.8±0.1, 10.7±0.1, 10.8±0.1, 13.3±0.1, 14.0±0.1, 15.1±0.1 degrees, which correspond respectively to d-spacing at 20.4, 11.1, 9.0, 8.3, 8.2, 6.6, 6.3 and 5.9 Angstroms (Å) ("Form 1").

Methods for preparing Compound A and pharmaceutical salts thereof include, but are not limited to, those described in WO/2007/028654, U.S. Pat. No. 8,093,242, and WO/2011/023733, the entireties of which are incorporated herein by reference.

Solubilizers

In some embodiments, the pharmaceutical formulation of the present disclosure comprises a solubilizer.

In some embodiments, the concentration of the solubilizer ranges from about 70% w/w to about 99.9% w/w, from about 75% w/w to about 99.7% w/w, from about 80% w/w to about 99.5% w/w, from about 85% w/w to about 99.2% w/w, or from about 90% w/w to about 99% w/w.

In some embodiments, the concentration of the solubilizer ranges from about 50% w/w to about 99% w/w, from about 55% w/w to about 95% w/w, from about 60% w/w to about 90% w/w, from about 65% w/w to about 85% w/w, from about 67% w/w to about 82% w/w, or from about 69% w/w to about 79% w/w.

In some embodiments, the concentration of the solubilizer ranges from about 35% w/w to about 95% w/w, from about 40% w/w to about 90% w/w, from about 45% w/w to about 85% w/w, from about 55% w/w to about 80% w/w, from about 60% w/w to about 75% w/w, or from about 62% w/w to about 72% w/w.

In some embodiments, the concentration of the solubilizer ranges from about 15% w/w to about 70% w/w, from about 20% w/w to about 65% w/w, from about 25% w/w to about 60% w/w, from about 30% w/w to about 55% w/w, from about 35% w/w to about 50% w/w, or from about 37% w/w to about 47% w/w.

In some embodiments, the concentration of the solubilizer ranges from about 15% w/w to about 60% w/w, from about 20% w/w to about 65% w/w, from about 20% w/w to about 55% w/w, from about 25% w/w to about 50% w/w, from about 30% w/w to about 45% w/w, or from about 32% w/w to about 42% w/w.

In some embodiments, the concentration of the solubilizer ranges from about 10% w/w to about 50% w/w, from about 15% w/w to about 45% w/w, from about 20% w/w to about 40% w/w, from about 22% w/w to about 37% w/w, or from about 24% w/w to about 34% w/w.

In some embodiments, the concentration of the solubilizer ranges from about 5% w/w to about 40% w/w, from about 8% w/w to about 35% w/w, from about 10% w/w to about 30% w/w, from about 12% w/w to about 27% w/w, or from about 14% w/w to about 24% w/w.

In some embodiments, the concentration of the solubilizer ranges from about 3% w/w to about 25% w/w, from about 4% w/w to about 20% w/w, from about 5% w/w to about 17% w/w, from about 6% w/w to about 14% w/w, or from about 7% w/w to about 13% w/w.

Suitable solubilizers include, but are not limited to, any one or mixture of [with CAS numbers shown in parentheses]: Anionic emulsifying wax [8014-38-8] also called Collone HV, Crodex A, Cyclonette Wax, Kerawax, Lanette SX, Lanette W. Benzalkonium chloride (alkyldimethyl(phenylmethyl) ammonium chloride [8001-54-5]) also called Hyamine 3500, Pentonium, Zephiran. Benzethonium chloride (N,N-Dimethyl-N-[2-[2-4-(1,1,3,3-tetramethylbutyl) phenoxy]ethoxy]ethyl]-benzene-methanaminium chloride [121-54-0], p-diisobutylphenoxyethoxyethyl dimethyl benzyl ammonium chloride monohydrate [5929-09-9]). Benzyl alcohol (benzenemethanol [100-51-6]). Benzyl benzoate (benzoic acid phenylmethyl ester [120-51-4]). Betadex sulfobutyl ether sodium (β-cyclodextrin sulfobutylether, sodium salt [182410-00-0]) also called ADVASEP-7, Capitsol. Cetylpyridinium chloride (1-hexadecylpyridinium chloride [123-05-5], 1-hexadecylpyridinium chloride monohydrate [6004-24-6]) also called Cepacol, Cepacol Chloride, Cetamiun, Dobendan, Medilave, Pristacin, Pyrisept. Cholestyramine Resin (cholestyramine [11041-12-6]) also called DUOLITE AP143, Purolite A430MR. Cyclodextrins (α-cyclodextrin [10016-20-3], β-cyclodextrin [7585-39-9], γ-cyclodextrin [17465-86-0]) also called Cavitron, Encapsin, Cavamax W6 Pharma, Cavamax W7 Pharma, Cavamax W8 Pharma, E459, Kleptose). Diethylene glycol monoethyl ether (2-(2-ethoxyethoxy)ethanol [111-90-0]) also called Carbitol, Transcutol HP, Transcutol P. Dimethyl-β-cyclodextrin (di-O-methyl-β-cyclodextrin [51166-71-3]). Fumaric acid ((E)-2-butenedioic acid [110-17-8]). Glyceryl monocaprylate (1,3-dihydroxy-2-propanyl octanoate [26402-26-6]) also called Imwitor 308. Glyceryl laurate (2,3-dihydroxypropyl dodecanoate [142-18-7]) also called Aldo MLD KFG, Cithrol GML, Colonial Monolaurin, Imwitor 312, Lauricidin, Lumulse GML K, Ultrapure GML. Glyceryl dilaurate (2-dodecanoyloxy-3-hydroxypropyl) dodecanoate [17598-94-6; 27638-00-2]) also called Capmul GD L. Glyceryl linoleate (2,3-dihydroxypropyl (9Z,12Z)-octadeca-9,12-dienoate [2277-28-3; 26545-74-4]) also called Maisine. Glyceryl monostearate (octadecanoic acid, monoester with 1,2,3-propanetriol [31566-31-1]) also called Capmul GMO-50K, Cutina GMS V, Dermowax GMS, DUBCARE GMS, Emalex GMS, Imwitor 191, Imwitor 491, Imwitor 900, Imwitor 900K, Kessco GMS, Lonzest GMS, Myvaplex 600P, Myvatex, Protachem GMS-450, Rheodol MS-165V, Starfol GMS, Stepan GMS, Tegin 90, Tegin 503, Tegin 515, Tegin 4100, Tegin M, Ultimate GMS. Mono- and di-glycerides of fatty acids (mainly caprylic and capric) (mono- and di-glycerides, glycerol monocaprylocaprate Type I, glyceryl monocaprlocaprate Type 1) also called Capmul MCM, Imwitor 988. Mono-, di and triglycerides of fatty acids [73398-61-5] also called Imwitor 742. Hydroxypropyl betadex (β-cyclodextrin, 2-hydroxypropyl ether [94035-02-6; 128446-35-5]) also called Cavasol W7 HP Pharma, Kleptose HPB. Hydroxyethyl-β-cyclodextrin (β-cyclodextrin, 2-hydroxyethyl ether [98513-20-3; 128446-32-2]). Hypromellose (cellulose, 2-hydroxypropyl methyl ether [9004-65-3]) also called Anycoat C, Benecel hypromellose, BonuCel, Headcel Cellulose, Mecellose, Methocel, Metolose, Pharmacoat, Rutocel, Vivapharm HPMC. Lanolin alcohols [8027-33-6] also called Argowax, Lanis AL, Lantrol 1780, Ritawax, Super Hartolan. Lecithin [8002-43-5; 8030-76-01; 93685-90-6] also called Coatsome NC, E322, Epikuron, Lecigran, Lipoid, Phosal 53 MCT, Phospholipon 100 H, ProKote LSC, Sternfine, Sternpur, Topcithin, Yelkin. Linoleic acid ((Z,Z)-9,12-octadecadienoic acid [60-33-3]) also called Emersol 310, Emersol 315, Pamolyn, Polylin No. 515. Meglumine (1-deoxy-1-(methylamino)-D-gluitol [6284-40-8]). Methylpyrrolidone (1-methylpyrrolidin-2-one [872-50-4]) also called M-Pyrol, Pharmasolve. Niacinamide (3-pyridinecarboxamide [98-92-0]) also called vitamin B3. Non-ionic emulsifying wax [97069-99-0] also called Collone NI, Crodex N, Emulgade 1000NI, Kerawax, Lipowax P, Masurf Emulisfying Wax, Permulgin D, Polawax, Ritachol 2000, T-Wax. Oleic acid ((Z)-9-octadecenoic acid [112-80-1]) also called Crodolene, Crossential 094, Emersol, Glycon, Groco, Hy-Phi, Industrene, Metaupon, Neo-Fat, Priolene. Oleyl alcohol ((Z)-9-octadecen-1-ol [143-28-2]) also called HD-Eutanol V PH, Novol, Ocenol. Phospholipids also called Coatsome, Lipoid, PhosphoLipid with specific examples Dilauroyl phosphatidylcholine [18194-25-7] also called Coatasome MC-2020, PhosphoLipid-DPAPC; Dimyristoyl phosphatidylcholine [18194-24-6] also called Coatasome MC-4040, Lipoid PC 14:0/14:0 (DMPC), PhospoLipid-DMPC; Dipalmitoyl phosphatidylcholine [63-89-8] also called Coatasome MC-6060, Lipoid PC 16:0/16:0 (DPPC), PhospoLipid-DPPC; Distearoyl phosphatidylcholine [816-94-4] also called Coatasome MC-8080, Lipoid PC 18:0/18:0 (DSPC), PhospoLipid-DSPC; Dioleoyl phosphatidylcholine [4235-95-4] also called Coatasome MC-8181, Lipoid PC 18:1/18:1 (DOPC), PhospoLipid-DOPC; Dierucoyl phosphatidylcholine [51779-95-4] also called PhospoLipid-DERPC; Palmitoyloleoyl phosphatidylcholine [26853-31-6] also called Coatasome MC-6081, PhospoLipid-POPC; Dimyristoyl phosphatidylglycerol, sodium salt [67232-80-8] also called Coatasome MG-4040LS, Lipoid PG 14:0/14:0 (D MPG), PhospoLipid-D MPG; Dipalmitoyl phosphatidylglycerol, sodium salt [67232-81-9] also called Coatasome MG-6060LS, Lipoid PG 16:0/16:0 (DPPG), PhospoLipid-DPPG; Distearoyl phosphatidylglycerol, sodium salt [67232-82-0] also called Coatasome MG-8080LS, Lipoid PG 18:0/18:0 (DSPG), PhospoLipid-DSPG; Dioleoyl phosphatidylglycerol, sodium salt [62700-69-0] also called Lipoid PG 18:1/18:1 (DOPG), PhospoLipid-DOPG; Palmitoyloleoyl phosphatidylglycerol, sodium salt [81490-05-3] also called Lipoid PG 16:0/18:1 (POPG), PhospoLipid-POPG; Dimyristoyl phosphatidylethanolamine [998-07-02] also called Coatasome ME-4040, Lipoid PE 14:0/14:0 (DMPE); Dipalmitoyl phosphatidylethanolamine [923-61-5] also called Coatasome ME-6060, Lipoid PE 16:0/16:0

(DPPE); Distearoyl phosphatidylethanolamine [1069-79-0] also called Coatasome ME-8080, Lipoid PE 18:0/18:0 (DSPE); Dioleoyl phosphatidylethanolamine [4004-05-1] also called Coatasome ME-8181, Lipoid PE 18:1/18:1 (DOPE); Dimyristoyl phosphatidic acid, sodium salt [80724-31-8] also called Coatasome MA-4040LS; Dipalmitoyl phosphatidic acid, sodium salt [74427-52-4] also called Coatasome MA-6060LS, Lipoid PA 16:0/16:0 (DPPA); Distearoyl phosphatidic acid, sodium salt [108321-18-2] also called Coatasome MA-8080LS, Lipoid PA 18:0/18:0 (DSPA); Dioleoyl phosphatidylserine, sodium salt [70614-14-1] also called Coatasome MS-8181LS. Polacrilex resin [copolymer of methacrylic acid and divinylbenzene [50602-21-6; 80892-32-6] also called Amberlite IRP-64. Poloxamers (α-hydro-ω-hydroxypoly(oxyethylene)poly(oxypropylene)poly(oxyethylene) block copolymer [9003-11-6]) also called Lutrol, Monolan, Pluracare, Pluronic, Supronic, Surfonic, Synperonic. Polymethacrylates also called Acryl-EZE, Drugcoat, Eastacryl, Eudragit, Kollicoat MAE with specific examples Poly(butyl methacrylate, (2-dimethylaminoethyl) methacrylate, methyl methacrylate) 1:2:1 [24938-16-7] also called Eudragit E 100, Eudragit E 12.5, Eudragit E PO; Poly(ethyl acrylate, methyl methacrylate) 2:1 [9010-88-2] also called Eudragit NE 30 D, Eudragit NE 40 D, Eudragit NM 30 D; Poly(methacrylic acid, methyl methacrylate) 1:1[25806-15-1] also called Eudragit L 100, Eudragit L 12.5; Poly(methacrylic acid, ethyl acrylate) 1:1 [25212-88-8] also called Acryl-EZE 93A, Acryl-EZE MP, Eudragit L 30 D-55, Eudragit L 100-55, Eastacryl 30D, Kollicoat MAE 30 DP, Kollicoat MAE 100 P; Poly(methacrylic acid, methyl methacrylate) 1:2 [25086-15-1] also called Eudragit S 100, Eudragit S 12.5, Eudragit FS 30D; Poly(ethyl acrylate, methyl methacrylate, methacrylic) 7:3:1 [33434-24-1] also called Eudragit RL 100, Eudragit RL PO, Eudragit RL 30 D, Eudragit RL 12.5, Eudragit RS 100, Eudragit RS PO, Eudragit RS 30 D, Eudragit RS 12.5. Polyoxyethylene alkyl ethers (polyethylene glycol monocetyl ether [9004-95-9], polyethylene glycol monolauryl ether [9002-92-01], polyethylene glycol monooley [9004-98-2] ether, polyethylene glycol monostearyl ether [9005-00-9]) also called Brij, Cremophor A, Cyclogol 1000, Emalex, Emulgen, Ethosperse, Genapol, Hetoxol, Hostacerin, Jeecol, Lipocol, Lumulse, Nikkol, Procol, Ritholeth, Ritox with specific examples Cetomacrogol 1000 also called Cresmer 1000; Polyoxyl 6 cetostearyl ether also called Ceteareth 6, Cremephor A6; Polyoxyl 20 cetostearyl ether also called Brij CS-20, Ceteareth 20, Cremephor A20 polyether, Genapol T200, Hetoxol CS-20, Jeecol CS-20, Lipocol SC-20, Lumulse CS-20, Ritacet 20; Polyoxyl 25 cetostearyl ether also called Brij CS25, Ceteareth 25, Cremephor A25, Hetoxol CS-25; Polyoxyl 2 cetyl ether also called Brij C2, Hetoxol CA-2, Jeecol CA-10, Lipocol C-2, Nikkol BC-2, Procol CA-2; Polyoxyl 10 cetyl ether also called Brij C10, Jeecol CA-10, Lipocol C-10, Nikkol BC-10TX, Procol CA-10; Polyoxyl 20 cetyl ether also called Brij C20, Hetoxol CA-20, Jeecol CA-20, Lipocol C-20, Nikkol BC-20TX; Polyoxyl 26 glyceryl ether also called Ethosperse G-26, Genapol G-260, Glycereth-26, Hetoxide G-26, Jeechem GL-26; Polyoxyl 4 lauryl ether also called Brij L4, Ethosperse LA-4, Genapol LA 040, Hetoxol LA-4, Jeecol LA-4, Lipocol L-4, Lumulse L-4, Nikkol BL-4.2, Procol LA-4; Polyoxyl 9 lauryl ether also called Brij L9, Hetoxol LA-9, Jeecol LA-9, Nikkol BL-9EX; Polyoxyl 12 lauryl ether also called Hetoxol LA-12, Jeecol LA-12, Lipocol L-12, Lumulse L-12, Procol LA-12; Polyoxyl 23 lauryl ether also called Brij L23, Ethosperse LA-23, Genapol LA 230, Hetoxol LA-23, Jeecol LA-23, Lipocol L-23, Lumulse L-23, Procol LA-23, Ritox 35; Polyoxyl 2 oleyl ether also called Brij O2, Genapol O 020, Jeecol OA-2, Lipocol O-2, Nikkol BO-2V, Procol OA-2, Ritoleth 2; Polyoxyl 10 oleyl ether also called Brij O10, Genapol O100, Hetoxol OA-10, Jeecol OA-10, Lipocol O-10, Nikkol BO-10V, Procol OA-10, Ritoleth 10; Polyoxyl 20 oleyl ether also called Brij O20, Genapol O 200, Jeecol OA-20, Lipocol O-20, Nikkol BO-20V, Procol OA-20, Ritoleth 20; Polyoxyl 2 stearyl ether also called Brij S2, Genapol HS 020, Hetoxol STA-2, Jeecol SA-2, Lipocol S-2, Nikkol BS-2, Procol SA-2; Polyoxyl 10 stearyl ether also called Brij S10, Hetoxol STA-10, Jeecol SA-10, Lipocol S-10, Procol SA-10; Polyoxyl 20 stearyl ether also called Brij S20, Jeecol SA-20, Lipocol S-20; Polyoxyl 21 stearyl ether also called Brij S721, Jeecol SA-21, Lipocol S-21, Ritox 721; Polyoxyl 100 stearyl ether also called Brij S100, Hetoxol STA-100, Jeecol SA-100. Polyoxyethylene castor oil derivatives (polyethoxylated castor oil [61791-12-6]) also called Acconon, Etocas, Eumulgin, Jeechem, Kolliphor, Lipocol, Lumulse, Nikkol, Protachem, Simulsol with specific examples Polyoxyl 5 castor oil also called Etocas 5, Hetoxide C-5, Jeechem CA-5, Lumulse CO-5; Polyoxyl 9 castor oil also called Jeechem CA-9, Protachem CA-9; Polyoxyl 15 castor oil also called Etocas 15, Jeechem CA-15, Protochem CA-15; Polyoxyl 35 castor oil also called Etocas 35, Super refined Etocas 35, Emulgin RO 35 PH, Kolliphor EL, Kolliphor ELP; Polyoxyl 40 castor oil also called Acconon CA-40, Croduret 40, Etocas 40, Eumulgin RO 40, Hetoxide C40, Jeechem CA-40, Lumulse CO-40, Marlowet R40, Nikkol CO 40TX, Protachem CA-40; Polyoxyl 40 hydrogenated castor oil also called Croduret 40, Eumulgin HRE 40PH, Hetoxide HC40, Jeechem CAH-40, Kolliphor RH 40, Lipocol HCO-40, Lipocol LAV HCO-40, Lumulse HCO 40, Nikkol HCO 40 Pharma, Protachem CAH-40; Polyoxyl 60 castor oil also called Jeechem CA-60, Nikkol CO 60TX; Polyoxyl 60 hydrogenated castor oil also called Croduret 60, Eumulgin HRE 60, Hetoxide HC60, Jeechem CAH-60, Kolliphor RH 60, Lipocol HCO-60, Nikkol HCO 60, Protachem CAH-60; Polyoxyl 100 castor oil also called Jeechem CA-100; Polyoxyl 100 hydrogenated castor oil also called Jeechem CA-100, Nikkol HCO 100; Polyoxyl 200 castor oil also called Hetoxide C200, Jeechem CA200; Polyoxyl 200 hydrogenated castor oil also called Jeechem CAH-200. Polyoxyethylene sorbitan fatty acid esters with specific examples Polysorbate 20 (polyoxyethylene 20 sorbitan monolaurate [9005-64-5]), also called Alkest TW20, Armotan PML20, Atmer 110, Cremophor PS 20, Crillet 1, Crillet 1 HP, Crillet 1 HPW, Drewmulse, Durfax 20, E432, Eumilgin SML 20, Glyosperse L-20, Hetsorb L-20E, Hodag PSML-20, Kaopan TW L120, Lamsorb SML-20, Liposorb L-20, Liposorb L-20K, Montanox 20, Nissan Nonion LT-221, Norfox Sorbo T20, POE-SML, Protasorb L-20-K, Ritabate 20, Sorbax PML-20, Sorgen TW-20, T-Maz 20, T-Maz 20K, Protasorb L-20, Tego SML-20, Tween 20, Tween 20HP, Tween 20L; Polysorbate 21 (polyoxyethylene (4) sorbitan monolaurate [9005-64-5]) also called Crillet 11, Hodag PSML-4, Protasorb L-5, Tween 21; Polysorbate 40 (polyoxyethylene 20 sorbitan monpalmitate [9005-66-7]) also called Atmer 112, Crillet 2, E434, Eumulgin SMP, Glyosperse S-20, Hodag-PSMP-20, Lamesorb SMP-20, Liposorb P-20, Lonzest SMP-20, Montanax 40, Protosorb P-20, Ritabate 40, Sorbax PMP-20, Tween 40; Polysorbate 60 (polyoxyethylene 20 sorbitan monostearate [9005-67-8]) also called Alkest TW 60, Atlas 70K, Atlas Armotan PMS 20, Cremophor PS-60, Crillet 3, Crillet 3HP, Crillet 3 Super, Drewpone 60K, Durfax 60, Durfax 60K, E435, Emrite 6125, Eumulgin SMS, Glyosperse S-20 KFG, Hetsorb S-20E, Hodag PSMS-20, Hodag SVS-18, Kaopan TWS120, Lamsorb SMS-20, Liposorb S-20, Liposorb S-20K, Lonzest SMS-20, Montanox 60, Nikkol TS-10, Norfox Sorbo T-60, Polycon T60K, Protsorb S-20, Ritabate 60, Sorbax PMS-20, T-Maz 60, T-max 60KHS, Tego SMS60, Tween 60, Tween 60K, Tween 60 Veg, Tween 60 VS; Polysorbate 61 (polyoxyethylene (4) sorbitan monostearate [9005-67-8]) also called Crillet 31 L02, Hetsorb S-4, Hodag PSMS-4, Liposorb S-4, Protasorb S-4, Tween 61, Tween 61 N, Tween 61 V, Tween 61 Veg; Polysorbate 65 (polyoxyethylene 20 sorbitan tristearate [9005-71-4]) also called Alkamuls PSTS-20, Crillet 35, E436, Glyosperse TS-20 KFG, Hodag-PSTS-20, Lamsorb STS-20, Lanzet STS-20, Liposorb TS-20, Montonax 65, Protasorb STS-20, Sorbax PTS-20, T-Maz 65K, Tween 65, Tween 65K, Tween 65 V; Polysorbate 80 (polyoxyethylene 20 sorbitan monooleate [9005-65-6]) also called Alkest TW 80, Atlas E, Atmer 116, Armotan PMO 20, Cremophor PS 80, Crillet 4, Crillet 4 HP, Crillet 4 Super, Crillet 50, Drewmulse POE-SMO, Drewpone 80K, Durfax 80, Durfax 80K, E433, Emrite 6120, Eumulgin SMO, Glyosperse 0-20, Hetsorb 0-20E, Hodag PSMO-20, Liposorb O-20, Liposorb O-20K, Montanox 80, Olethytan 20, Polysorbat 80, Protasorb O-20, Ritabate 80, Sepitrap 80, Tego SMO-80, Tego SMO-80V, Tween 80, Tween 80 HP, Tween 80K, Tween 80 LM, Tween 80 SP, Tween 80 V, Tween 80 Veg; Polysorbate 81 (polyoxyethylene (5) sorbitan monooleate [9005-65-6]) also called Crillet 41, Hetsorb-O5E, Hodag PSMO-5, Protsorb O-5, Sorbax PMO-5, T-Maz 81, Tego SMO 81, Tween 81, Tween 81N; Polysorbate 85 (polyoxyethylene 20 sorbitan trioleate [9005-70-3]) also called Alkamuls PSTO-20, Atmer 118, Crillet 45, Crillet 45LD, Glyosperse TO-20, Hetsorb TO-20E, Hodag PSTO-20, Liposorb TO-20, Lonzest STO-20, Montanox 85, Protasorb TO-20, Sorbax PTO-20, Tego STO 85, Tween 85, Tween 85LM, Tween 85N, Tween 85V; Polysorbate 120 (polyoxyethylene 20 sorbitan monoisostearate [66794-58-9]) also called Crillet 6. Polyoxyl 15 hydroxystearate (2-hydroxyethyl-12-hydroxyoctadecanoate [70142-34-6]) also called Solutol HS 15. Polyoxylglycerides with specific examples Caprylocaproyl polyoxylglycerides [73398-61-5; 223129-75-7] also called caprylocaproyl polyoxyl-8 glycerides, DUBCARE GPE 810, Labrasol ALF; Lauroyl polyoxylglycerides [57107-95-6] also called lauroyl polyoxyl-6 glycerides Gelucire 44/14, Labrafil M2130CS; Linoleoyl polyoxylglycerides [61789-25-1] also calledlinoleoyl polyoxyl-6 glycerides, Labrafil M2125CS; Oleoyl polyoxylglycerides [68424-61-3; 9004-96-0] also called oleoyl polyoxyl-6 glycerides, DUBCARE OLGA SF, Labrafil M1944CS; Stearoyl polyoxylglycerides [1323-83-7; 9005-08-07] also called stearoyl polyoxyl-32 glycerides, Gelucire 50/13, Simulsol L165 PHA. Polyvinyl acetate phthalate [34481-48-6]. Povidone (1-ethenyl-2-pyrrolidinone homopolymer [9003-39-8]) also called E1201, Kollidon, Plasdone, Povipharm. Propylene glycol dilaurate (2-dodecanoyloxypropyl dodecanoate [22788-19-9]) also called Capmul PG-2L, E477, Emalex PG di-L. Propylene glycol monolaurate (1,2-propanediol monolaurate [27194-74-7; 142-55-2]) also called Capmul PG-12, Cithrol PGML, E-477, Emalex PGML, Imwitor 412, Lauroglycol 90, Lauroglycol FCC, Schercemol PGML, STELLIESTERS LPG. Pyrrolidone (2-pyrrolidinone [616-45-5]) also called Kollisolv PYR, Soluphor P. Sodium Bicarbonate (carbonic acid monosodium salt [144-55-8]) also called E500, Effer-Soda. Sodium lauryl sulfate (sulfuric acid monododecyl ester sodium salt (1:1) [151-21-3]) also called Elfan 240, Texapon K12P. Sodium polystyrene sulfonate (divinylbenzene copolymer with styrene, sulfonated, sodium salt [63182-08-1]) also called AMBERLITE IRP69, Kayexalate, Kionex, Resonium A, Solystat Sorbitan esters with specific examples Sorbitan diisostearate (sorbitan diisooctadecanoate [68238-87-9]); Sorbitan dioleate ((Z,Z)-sorbitan di-9-octadecanoate [29116-98-1]); Sorbitan monoisostearate (sorbitan monoisooctadecanoate [71902-01-7]) also called Arlacel 987, Crill 6, Montane 70; Sorbitan monolaurate (sorbitan monododecanoate [1338-39-2]) also called Alkamuls SML, Arlacel 20, Armotan ML, Crill 1, Dehymuls SML, E493, Emsorb 2515, Glycomul L, Hodag SML, Liposorb L-80, Montane 20, Protachem SML, Sorbester P12, Sorbirol L, Span 20, Tego SML; Sorbitan monooleate ((Z)-sorbitan mono-9-octadecenoate [1338-43-8]) also called Ablunol S-80, Alkamuls SMO, Arlacel 80, Armotan MO, Capmul O, Crill 4, Crill 50, Dehymuls SMO, Drewmulse SMO, Drewsorb 80K, E494, Glycomul O, Emsorb 2500, Glycomul O, Hodag SMO, Lamesorb SMO, Liposorb O, Montane 80, Nikkol SO-10, Nissan nonion OP-80R, Norfox Sorbo S-80, Polycon S80 K, Protosorb SMO, Protachem SMO, S-Maz 80K, Sorbester P17, Sorbirol O, Sorgen 40, Sorgen S-40-H, Span 80, Tego SMO; Sorbitan monopalmitate (sorbitan monohexadecanoate [26266-57-9]) also called Ablunol S-40, Arlacel 40, Armotan MP, Crill 2, Dehymuls SMP, E495, Glycomul P, Hodag SMP, Lamesorb SMP, Liposorb P, Montane 40, Nikkol SP-10, Nissan nonion PP-40R, Protachem SMP, Protosorb SMP, Sorbester P16, Sorbirol P, Span 40; Sorbitan monostearate (sorbitan monooctadecanoate [1338-41-6]) also called Ablunol S-60, Alkamuls SMS, Arlacel 60, Armotan MS, Atlas 110K, Capmul S, Crill 3, Dehymuls SMS, Drewmulse SMS, Drewsorb 60K, Durtan 60, Durtan 60K, E491, Famodan MS Kosher, Glycomul S FG, Glycomul S KFG, Hodag SMS, Lamesorb SMS, Liposorb S, Liposorb SC, Liposorb S-K, Montane 60, Nikkol SP-60R, Norfox Sorbo S-60FG, Polycon S60K, Protachem SMS, Prote-sorb SMS, S-Maz 60K, S-Maz 60KHS, Sorbester P18, Sorbirol S, Sorgen 50, Span 60, Span 60K, Span 60 VS, Tego SMS; Sorbitan sesquiisostearate (sorbitan sesquiisooctadecanoate [71812-38-9]) also called Protachem SQI; Sorbitan sesquioleate ((Z)-sorbitan sesqui-9-octadecanoate [8007-43-0]) also called Arlacel C, Arlacel 83, Crill 43, Glycomul SOC, Hodag SSO, Liposorb SQO, Montane 83, Nikkol SO-15, Nissan nonion OP-83RAT, Protachem SOC, Sorgen 30, Sorgen 30, Sorgen S-30-H; Sorbitan sesquistearate (sorbitan sesquioctadecanoate [51938-44-4]); Sorbitan triisostearate (sorbitan triisooctadecanoate [54392-27-7]); Sorbitan trilaurate (sorbitan tridodecanoate [71217-21-5]) also called Span 25; Sorbitan trioleate ((Z,Z,Z)-sorbitan tri-9-octadecenoate [26366-58-0]) also called Ablunol S-85, Arlacel 85, Crill 45, Glycomul TO, Hodag STO, Liposorb TO, Montane 85, Nissan nonion OP-85R, Protachem STO, Prote-sorb STO, S-Maz 85K, Sorbester P37, Span 85, Tego STO; Sorbitan tristearate (sorbitan tri-octadecanoate [26658-19-5]) also called Alkamuls STS, Crill 35, Crill 41, Drewsorb 65K, E492, Famodan TS Kosher, Glycomul TS KFG, Hodag STS, Lamesorb STS, Liposorb TS, Liposorb TS-K, Montane 65, Protachem STS, Prote-sorb STS, Sorbester P38, Span 65, Span 65K. Stearic acid (octadecanoic acid [57-11-4]) also called Crodacid E570, Cristal G, Cristal S, Dermofat 4919, Dervacid, DUB CARE STEA, E570, Edenor, Emersol, Extra AS, Extra P, Extra S, Extra ST, Hystrene, Industrene, Kortacid 1895, Pearl Steric, Pristerene, Speziol L2SM GF, Stellipress Micro, Tegostearic, TriStar. Sucrose palmitate ([6-[3,4-dihydroxy-2,5-bis(hydroxymethyl)oxlan-2-yl]oxy-3,4,5-trihydroxyoxan-2-yl] methyl hexadecanoate [26446-38-8])) also called E473, Ryoto, Sisterna PS750-C, STELLIESTERS SE 15P, Surfhope SE Cosme, Surfhope SE Pharma. Sucrose stearate (sucrose monostearate [25168-73-4]; sucrose distearate [27195-16-0]; sucrose tristearate [27923-63-3])) also called Crodesta F, E473, Sisterna SP, STELLIESTERS SE 5S, Surfhope SE, Tegosoft TE. Tricaprylin (1,3-di(octanoyloxy) propan-2-yl octanoate [538-23-8]) also called Captex 8000, Hest TC, Miglyol 808, Rofetan GTC, Trivent OC-G. Trimethyl-β-cyclodextrin (tri-O-methyl-β-cyclodextrin [55216-11-0]). Triolein (2,3-bis[[(Z)-octadec-9-enoyl]oxy]propyl (Z)-octadec-9-enoate [122-32-7] also called Captex GTO. Vitamin E polyethylene glycol succinate (4-O-(2-hydroxyethyl-1-O-[2,5,7,8-tetramethyl-2-(4,8,12-trimethyltridecyl)-3,4-dihydrochromen-6-yl)butanedioate [9002-96-4; 30999-06-5]) also called Speziol TPGS Pharma, VEGS.

In some embodiments, the solubilizer is selected from Caprylocaproyl polyoxyl-8 glycerides (Labrasol ALF), Glycerol Monocaprylocaprate (Capmul MCM), Polyoxyl 35 castor oil (Kolliphor EL), Polysorbate 80 (Tween 80), and mixtures thereof.

In some embodiments, the solubilizer is Caprylocaproyl polyoxyl-8 glycerides (Labrasol ALF).

In some embodiments, the concentration of the Caprylocaproyl polyoxyl-8 glycerides (Labrasol ALF) ranges from about 70% w/w to about 99.9% w/w, from about 75% w/w to about 99.7% w/w, from about 80% w/w to about 99.5% w/w, from about 85% w/w to about 99.2% w/w, or from about 90% w/w to about 99% w/w.

In some embodiments, the solubilizer is a mixture of Glycerol Monocaprylocaprate (Capmul MCM) and Polyoxyl 35 castor oil (Kolliphor EL).

In some embodiments, the concentration of the Glycerol Monocaprylocaprate (Capmul MCM) ranges from about 50% w/w to about 99% w/w, from about 55% w/w to about 95% w/w, from about 60% w/w to about 90% w/w, from about 65% w/w to about 85% w/w, from about 67% w/w to about 82% w/w, or from about 69% w/w to about 79% w/w. In some embodiments, the concentration of the Polyoxyl 35 castor oil (Kolliphor EL) ranges from about 5% w/w to about 40% w/w, from about 8% w/w to about 35% w/w, from about 10% w/w to about 30% w/w, from about 12% w/w to about 27% w/w, or from about 14% w/w to about 24% w/w.

In some embodiments, the solubilizer is a mixture of Glycerol Monocaprylocaprate (Capmul MCM) and of the Polyoxyl 35 castor oil (Kolliphor EL), wherein the concentration of, the concentration of the Monocaprylocaprate (Capmul MCM) ranges from 67% w/w to 82% and the concentration of the Polyoxyl 35 castor oil (Kolliphor EL) ranges from about 5% w/w to about 30% w/w, In some embodiments, the solubilizer is a mixture of Glycerol Monocaprylocaprate (Capmul MCM) and Caprylocaproyl polyoxyl-8 glycerides (Labrasol ALF).

In some embodiments, the concentration of the Glycerol Monocaprylocaprate (Capmul MCM) ranges from about 35% w/w to about 95% w/w, from about 40% w/w to about 90% w/w, from about 45% w/w to about 85% w/w, from about 55% w/w to about 80% w/w, from about 60% w/w to about 75% w/w, or from about 62% w/w to about 72% w/w. In some embodiments, the concentration of the Caprylocaproyl polyoxyl-8 glycerides (Labrasol ALF) ranges from about 10% w/w to about 50% w/w, from about 15% w/w to about 45% w/w, from about 20% w/w to about 40% w/w, from about 22% w/w to about 37% w/w, or from about 24% w/w to about 34% w/w.

In some embodiments, the solubilizer is a mixture of Glycerol Monocaprylocaprate (Capmul MCM) and Caprylocaproyl polyoxyl-8 glycerides (Labrasol ALF), wherein the concentration of the Glycerol Monocaprylocaprate (Capmul MCM) ranges from about 40% w/w to about 75% w/w and the concentration of the Caprylocaproyl polyoxyl-8 glycerides (Labrasol ALF) ranges from 15% w/w to about 40% w/w.

In some embodiments, the solubilizer is a mixture of Glycerol Monocaprylocaprate (Capmul MCM) and Polysorbate 80 (Tween 80).

In some embodiments, the concentration of the Glycerol Monocaprylocaprate (Capmul MCM) ranges from about 15% w/w to about 70% w/w, from about 20% w/w to about 65% w/w, from about 25% w/w to about 60% w/w, from about 30% w/w to about 55% w/w, from about 35% w/w to about 50% w/w, or from about 37% w/w to about 47% w/w. In some embodiments the concentration of the Polysorbate 80 (Tween 80) ranges from about 3% w/w to about 25% w/w, from about 4% w/w to about 20% w/w, from about 5% w/w to about 17% w/w, from about 6% w/w to about 14% w/w, or from about 7% w/w to about 13% w/w.

In some embodiments, the solubilizer is a mixture of Glycerol Monocaprylocaprate (Capmul MCM) and Polysorbate 80 (Tween 80), wherein the concentration of the Monocaprylocaprate (Capmul MCM) ranges from 30% w/w to 42% w/w, and the concentration of the Polysorbate 80 (Tween 80) ranges from 9% w/w to 10% w/w.

In some embodiments, the solubilizer is a mixture of Glycerol Monocaprylocaprate (Capmul MCM), Caprylocaproyl polyoxyl-8 glycerides (Labrasol ALF), and Polysorbate 80 (Tween 80).

In some embodiments, the concentration of the Glycerol Monocaprylocaprate (Capmul MCM) ranges from about 15% w/w to about 60% w/w, from about 20% w/w to about 65% w/w, from about 20% w/w to about 55% w/w, from about 25% w/w to about 50% w/w, from about 30% w/w to about 45% w/w, or from about 32% w/w to about 42% w/w. In some embodiments, the concentration of the Caprylocaproyl polyoxyl-8 glycerides (Labrasol ALF) ranges from about 3% w/w to about 25% w/w, from about 4% w/w to about 20% w/w, from about 5% w/w to about 17% w/w, from about 6% w/w to about 14% w/w, or from about 7% w/w to about 13% w/w. In some embodiments, the concentration of the Polysorbate 80 (Tween 80) ranges from about 3% w/w to about 25% w/w, from about 4% w/w to about 20% w/w, from about 5% w/w to about 17% w/w, from about 6% w/w to about 14% w/w, or from about 7% w/w to about 13% w/w.

In some embodiments, the solubilizer is a mixture of Glycerol Monocaprylocaprate (Capmul MCM), Caprylocaproyl polyoxyl-8 glycerides (Labrasol ALF), and Polysorbate 80 (Tween 80), wherein the concentration of the Glycerol Monocaprylocaprate (Capmul MCM) ranges from 30 w/w to 40% w/w, the concentration of Caprylocaproyl polyoxyl-8 glycerides (Labrasol ALF) ranges from 9% w/w to 10% w/w, the concentration of the Polysorbate 80 (Tween 80) ranges from 9% w/w to 10% w/w.

The solubilizers according to the invention are commercially available. Thus, for example Monocaprylocaprate (Capmul MCM) is available from Abitec Corporation, Janesville, Wis., USA; Caprylocaproyl polyoxyl-8 glycerides (Labrasol ALF) is available from Gattefossé, Saint Priest, France; Polysorbate 80 (Tween 80) is available from Croda Inc, Mill Hall, Pa., USA; and Polyoxyl 35 castor oil (Kolliphor EL) is available from BASF SE, Ludwigshafen, Germany.

Emulsifiers

In some embodiments, the pharmaceutical formulation of the present disclosure comprises an emulsifier.

In some embodiments, the concentration of the emulsifier ranges from about 15% w/w to about 70% w/w, from about 20% w/w to about 65% w/w, from about 25% w/w to about 60% w/w, from about 30% w/w to about 55% w/w, from about 35% w/w to about 50% w/w, or from about 38% w/w to about 48% w/w.

In some embodiments, the concentration of the emulsifier ranges from about 15% w/w to about 60% w/w, from about 20% w/w to about 65% w/w, from about 20% w/w to about 55% w/w, from about 25% w/w to about 50% w/w, from about 30% w/w to about 45% w/w, or from about 33% w/w to about 43% w/w.

Suitable emulsifiers include, but are not limited to, any one of mixture of [with CAS numbers shown in parentheses]: Acacia [9000-01-5]. Agar [9002-18-0]. Ammonium alginate [9005-34-9]. Ammonium glycrrhizate (α-D-glucopyranosiduric acid, (3β,20β)-20-carboxy-11-oxo-30-norlean-12-en-3-yl-2-O-β-D-glucopyranuronosyl-monoammonium salt; anhydrous [53956-04-0]; (α-D-glucopyranosiduric acid, (3β,20β)-20-carboxy-11-oxo-30-norlean-12-en-3-yl-2-O-β-D-glucopyranuronosyl-, monoammonium salt; pentahydrate [1407-03-0]) also called Magnasweet. Calcium alginate [9005-35-0] also called Calginate, Kaltostat. Calcium stearate (octadecanoic acid calcium salt [1592-23-0]) also called Ceasit PC, Kemistab EC-F, Synpro. Capric acid [334-48-5]. Carbomer ([9003-01-4] alternative names (carbomer 934 [9007-16-3]; carbomer homopolymer Type C [9007-17-4]; carbomer 941 [9062-04-08]; carbomer carboxypolymethylene [9007-20-9])) also called Acrypol, Acritamer, Carbopol, Pemulen, Tego Carbomer. Ceratonia (carob gum [9000-40-2]) also called Meyprofleur. Cetostearyl alcohol [67762-27-0; 8005-44-5] also called Crodacol CS90, DUB SC 20D, Kolliwax CSA, Lanette O, Speziol C16-18 Pharma, Tego Alkanol 1618, Tego Alkanol 6855. Cetyl alcohol (hexadecane-1-ol [36653-82-4]) also called Avol, Cachalot, Cetanol, Crodacol C70, Crodacol C90, Crodacol C95, HallStar CO-1695, Hyfatol 16-95, Kessco CA, Lanette 16, Lipocol C, Nacol 16-95, Rita CA, Speziol C16 Pharma, Tego Alkanol 16, Vegarol 1695, Vegarol 1698. Cetyl palmitate (hexadcyl hexadecanoate [540-10-3]) also called Crodamol CP, DUB CARE PC, Dynacerin CP, Estol 3694, Hallstar 653, Kessco CP, Palmil C, Pelemol CP, Sabowax CP, Stepan 653. Cholesterol (cholest-5-en-3β-ol [57-88-5]). Colophony ((2R,3S,4S,5R,6R)-2-(hydroxymethyl)-6-[E]-3-phenylprop-2-enoxy]oxane-3,4,5-triol [8050-09-7; 8050-10-0]). Diethanolamine (2,2'-iminobisethanol [111-42-2]). Glyceryl monooleate (9-octadecenoic acid (Z), monoester with 1,2,3-propane-triol [25496-72-4]) also called Aldo MO, Capmul GMO, Drewmulse GMO, DUB OG, DUBCARE OG, Hallstar GMO, Inwitor 948, Kessco GMO, Ligalub, Monomuls 90-018, Peceol. Hydrogenated Palm Oil [68514-74-9; 8033-29-2] also called Cegesoft, Dynasan P60, Softisan 154. Hydroxypropyl cellulose (cellulose, 2-hydroxypropyl ether [9004-62-2]) also called Aero Whip, Coatcel, Klucel, Nisso HPC. Hydroxypropyl starch [113894-92-1]). Lanolin (anhydrous lanolin [8006-54-0]) also called Coronet, E913, Lanis, Lantrol 1650, Pharmalan, Protalan anhydrous. Lanolin, hydrous [8020-86-4]. Lauric acid (dodecanoic acid [143-07-7]) also called C-1297, Hydrofol acid 1255, Hydrofol acid 1295, Hystrene 9512, Kortacid 1299, Lunac L70, Neo-fat 12, Neo-fat 12-43, Ninol AA62 Extra, Prifac 2920, Univol U314, Wecoline 1295. Magnesium oxide [1309-48-4] also called Descote, E530, Magcal, Magchem 100, Magnyox, Marmag, Oxymag. Medium-chain triglycerides [438544-49-1] also called Bergabest, Captex 300, Captex 355, Coconad, Crodamol GTCC, Delios, Kollisolv MCT, Labrafac CC, Labrafac Lipo, Labrafac WL1349, Miglyol 810, Miglyol 812, Myritol, Neobee M5, Nesatol, ProKote 2855, Stelliesters MCT, Waglinol 3/9280. Methylcellulose (cellulose methyl ester [9004-67-5] also called Benecel, BonuCel, Cellacol, Culminal MC, E461, Mapolose, Methocel, Metolose, Rutocel A 55 RT, Tylose, Viscol. Mineral oil [8012-95-1] and lanolin alcohols [8027-33-6] also called Amerchol L-101, Protalan M-16, Protalan M-26, Vilvanolin. Modified starch (includes acetylated distarch adipate [65996-63-6]; acid-treated waxy corn starch [68909-37-5]; distarch phosphate, waxy corn basis [55963-33-2]; oxidized waxy corn starch [65996-62-5]; sodium octenyl succinate starch [66829-29-6]) also called Amprac, C*Pharm, Capsul, Clearam, Cleargum, E1401-1452, Hi-Cap, Instant Pure-Cote, Lycoat, Pure-Cote, Pure-Gel, Purity, Purity Gum, Uni-Pure. Monoethanolamine (2-aminoethanol [141-43-5]). Myristic acid (tetradecanoic acid [544-63-8] also called Edenor C14 98-100. Myristyl alcohol (tetradecan-1-ol 112-72-1]) also called Dytol R-52, Lanette Wax KS, Lorol C14-95, Loxanol V, Nacol 14-95, Nacol 14-98, Unihydag WAX-14. Octyldodecanol [5333-42-6] also called Euthanol G PH, Jarcol 1-20, Jeecol ODD, STELLIESTERS ODOL. OSA modified gum acacia [455885-22-0]. Palmitic acid (hexadecanoic acid [57-10-13]) also called Edenor C16 98-100, Emersol 140, Emersol 143, Hydrofol, Hystrene 9016, Industrene 4516, Lunac P-95. Pectin [9000-69-5]) also called E440, Genu, Unipectine U. Polycarbophil [9003-97-8] also called Noveon AA-1. Polyoxyethylene stearates (polyoxyethylene stearate [9004-99-3]; polyoxyethylene distearate [9005-08-7]) also called Marlosol with specific examples Polyoxyl 2 stearate also called Hodag DGS, Lipo DGS, Lipopeg 2-DEGS; Polyoxyl 4 stearate also called Acconon 200-MS, Hodag 20-S, Lipopeg 2-DEGS, Protamate 200-DPS; Polyoxyl 6 stearate also called Cerasynt 616, DUB SPEG, Kessco PEG 300 Monostearate, Lipal 300S, Lipopeg 3-S, Polystate C, Protamate 300-DPS; Polyoxyl 8 stearate also called Acconon 400-MS, Cerasynt 660, Cithrol 4MS, Crodet S8, Emerest 2640, Grocor 400, Hodag 40-S, Kessco PEG-400 Monostearate, Lipopeg 4-S, Myrj 45, Pegosperse 400 MS, Protamate 400-DPS, Ritapeg 400 MS; Polyoxyl 12 stearate also called Hodag 60-S, Kessco PEG-600 Monostearate, Lipopeg 6-S, Pegosperse 600 MS, Protamate 600-DPS; Polyoxyl 20 stearate also called Cerasynt 840, Hodag 100-S, Kessco PEG-1000 Monostearate, Lipopeg 10-S, Myrj 49, Pegosperse 1000MS, Protomate 1000-DPS; Polyoxyl 30 stearate also called Myrj 51; Polyoxyl 40 stearate also called Crodet S40, E431, Emerest 2672, Hodag POE (40) MS, Lipal 395, Lipopeg 39-S, Myrj 52, Protamate 2000-DPS, Ritox 52, Simusol M52; Polyoxyl 50 stearate also called Atlas G-2153, Crodet S50, Lipal 505, Myrj 53; Polyoxyl 100 stearate also called Lipopeg 100-S, Myrj 59, Protomate 4400-DPS, Ritox 53; Polyoxyl 150 stearate also called Hodag 600-S, Ritox 59; Polyoxyl 4 distearate also called Hodag 22-S; Polyoxyl 8 distearate also called Hodag 42-S, Kessco PEG 400 DS, Protamate 400-DS; Polyoxyl 12 distearate also called Hodag 62-S, Kessco PEG 600 Distearate, Protamate 600-DS; Polyoxyl 32 distearate also called Hodag 154-S, Kessco PEG 1540 Distearate; Polyoxyl 150 distearate also called Hodag 602-S, Kessco PEG 6000 DS, Lipopeg 6000DS, Protamate 6000-DS. Potassium alginate [9005-36-1] also called Improved Kelmar, Protanal. Propylene glycol alginate [9005-37-2] also called E405, Kelcoloid, Kimiloid, Manucol Ester, PGA, Profoam, TIC Pretested. Safflower glycerides [79982-97-1].

Saponite [1319-41-1] also called Afrodit, Imvite 1016, Ionite P, Laponite, SapCa-1, Smectiton SA, SMI 200H, Stevensonite, Sumecton 5A, 5Y 5, Veegum S6198. Sodium borate (disodium tetraborate decahydrate [1303-96-4]) also called E285. Sodium citrate dihydrate (trisodium 2-hydroxy-propane-1,2,3-tricarboxylate dihydrate [6132-0403]). Sodium lactate [72-17-3] also called E325, Lacolin, Patlac, Purasal, Ritalac NAL. Sodium stearate (sodium octadecenoate [822-16-2]) also called Kemilub ES, Prodhygine, STELLIESTERS SE SS. Stearyl alcohol (1-octadecanol [112-92-5]) also called Alfol 18, Cachalot, Crodacol S95, Hyfatol 18-95, Hyfatol 18-98, Kolliwax SA, Lanette 18, Lipocol S, Nacol 18-94, Nacol 18-98, Nacol 18-99, Rita SA, Speziol C18 Pharma, Stearol, Stenol, Tego Alkanol 18, Vegarol 1895, Vegarol 1898. Tragacanth (tragacanth gum [9000-65-1]) also called E413. Triethanolamine (2,2',2''-nitrilotriethanol [102-71-6]) also called Tealan. Xanthan gum [11138-66-2] also called Grindsted, Keldent, Keltrol, Rhodicare S, Rhodigel, Rhodopol, Satiaxane U, Vanzan NF, Xantural.

In some embodiments, the emulsifier is Glyceryl Monooleate (Peceol).

In some embodiments, the concentration of the Glyceryl Monooleate (Peceol) ranges from about 15% w/w to about 70% w/w, from about 20% w/w to about 65% w/w, from about 25% w/w to about 60% w/w, from about 30% w/w to about 55% w/w, from about 35% w/w to about 50% w/w, or from about 38% w/w to about 48% w/w.

In some embodiments, the concentration of the Glyceryl Monooleate (Peceol) ranges from about 15% w/w to about 60% w/w, from about 20% w/w to about 65% w/w, from about 20% w/w to about 55% w/w, from about 25% w/w to about 50% w/w, from about 30% w/w to about 45% w/w, or from about 33% w/w to about 43% w/w.

The emulsifiers according of the invention are commercially available. Thus, for example Glyceryl Monooleate (Peceol) is commercially available from Gattefossé, Saint Priest, France.

Antioxidants

In some embodiments, the pharmaceutical formulation of the present disclosure comprises an antioxidant.

In some embodiments, the concentration of the antioxidant ranges from about 0.02% w/w to about 5% w/w, from about 0.05% w/w to about 4% w/w, from about 0.1% w/w to about 3% w/w, from about 0.2% w/w to about 2% w/w, from about 0.3% w/w to about 1.8% w/w, or from about 0.5% w/w to about 1.5% w/w.

In some embodiments, the concentration of the antioxidant ranges from about 0.005% w/w to about 3% w/w, from about 0.01% w/w to about 2% w/w, from about 0.02% w/w to about 1% w/w, from about 0.05% w/w to about 0.5% w/w, from about 0.08% w/w to about 0.4% w/w, or from about 0.1% w/w to about 0.3% w/w.

In some embodiments, the concentration of the antioxidant ranges from about 0.002% w/w to about 2% w/w, from about 0.005% w/w to about 1% w/w, from about 0.01% w/w to about 0.5% w/w, from about 0.02% w/w to about 0.3% w/w, from about 0.03% w/w to about 0.2% w/w, or from about 0.05% w/w to about 0.15% w/w.

In some embodiments, the concentration of the antioxidant ranges from about 0.0005% w/w to about 1% w/w, from about 0.001% w/w to about 0.5% w/w, from about 0.002% w/w to about 0.2% w/w, from about 0.005% w/w to about 0.1% w/w, from about 0.01% w/w to about 0.05% w/w, or from about 0.02% w/w to about 0.04% w/w.

Suitable antioxidants include, but are not limited to, any one or mixture of [CAS numbers shown in parentheses]: Acetone sodium bisulfite (2-hydroxy-2-propanesulfonic acid, sodium salt [540-92-1]). Alpha tocopherol (a racemic mixture (±)-(2RS,4'RS,8'RS)-2,5,7,8-tetramethyl-2-(4',8',12'-trimethyltridecyl)-6-chromanol [10191-41-0])—also called DL-alpha tocopherol, and the naturally occurring form D-alpha tocopherol (2R,4'R,8'R)-alpha-tocopherol)) also called Copherol F1300, E307, Vitamin E. Ascorbic acid (L-(+)-ascorbic acid [50-81-7]) also called C-97, E300. Ascorbyl palmitate (L-ascorbic acid 6-hexdecanoate [137-66-6]) also called E304). Butylated hydroxyanisole (BHA) (2-tert-butyl-4-methoxyphenol [25013-16-5]) also called E320, Nipanox BHA, Nipantiox 1-F, Tenox BHA. Butylated hydroxytoluene (BHT) (2,6-di-tert-butyl-4-methylphenol [128-37-0] also called Agidol, Dalpac, E321, Embanox BHT, Impruvol, Ionol CP, Nipanox BHT, OHS28890, Sustane, Tenox BHT, Topanol, Vianol. Carbon dioxide [124-38-9] also called E290. Citric acid monohydrate (2-hydroxy-1,2,3-propanetricarboxylic acid monohydrate [5949-29-1] also called E330. Dodecyl gallate (dodecyl 3,4,5-trihydroxybenzoate [1166-52-5]) also called E312, Nipagallin LA, Progallin LA. Erythorbic acid (D-isoascorbic acid [89-65-6]) also called E315. Ethyl oleate ((Z)-9-octadecenoic acid, ethyl ester [111-62-6]) also called Crodamol EO, DUB-CARE OE, Kessco Ea Histidine ((S)-2-amino-3-(imidazol-4-yl)propanoic acid [71-00-1]) also called Ajipure. Malic acid (hydroxybutanedioic acid [6915-15-7; (RS)-(±)-hydroxybutanedioic acid [617-48-1]) also called E296. D-Mannose ((3S,4S,5S,6R)-6-(hydroxymethyl)oxane-2,3,4,5-tetrol [3458-28-4] also called MannoTab. Monothioglycerol (3-mercapto-1,2-propanediol [96-27-5]). Niacinamide (3-pyridinecarboxamide [98-92-0]). Octyl gallate (octyl 3,4,5-trihydroxybenzoate [1034-01-1]) also called E311. Phosphoric acid (orthophosphoric acid [7664-38-2]) also called E338. Potassium metabisulfite (dipotassium pyrosulfite [16731-55-8]) also called E224. Propionic acid [79-09-4] also called E280. Propyl gallate (3,4,5-trihydroxybenzoic acid propyl ester [121-79-9]) also called E310, Progallin P, Tenox PG. Sodium ascorbate (monosodium L-(+)-ascorbate [134-03-2] also called E301, SA-99. Sodium formaldehyde sulfoxylate ([149-44-0]; sodium formaldehyde sulfoxylate dihydrate [6035-47-8]) also called Rongalite. Sodium metabisulfite (sodium pyrosulfite [7681-57-4]) also called E221. Sodium sulfite [7757-83-7] also called E221. Sodium thiosulfate (sodium thiosulfate anhydrous [7772-98-7]; sodium thiosulfate pentahydate [10102-17-7]) also called Ametox, Sodothiol, Sulfothiorine. Sulfur dioxide [7446-09-05] also called E220. Thymol ([89-83-8]; m-thymol [3228-0303]) also called Flavinol, Intrasol, Medophyll.

In some embodiments, the antioxidant is selected from DL-Alpha tocopherol (Vitamin E), butylated hydroxytoluene (BHT), and butylated hydroxyanisole (BHA), and mixtures thereof.

In some embodiments, the antioxidant is butylated hydroxytoluene (BHT).

In some embodiments, the concentration of the butylated hydroxytoluene (BHT) ranges from about 0.0005% w/w to about 1% w/w, from about 0.001% w/w to about 0.5% w/w, from about 0.002% w/w to about 0.2% w/w, from about 0.005% w/w to about 0.1% w/w, from about 0.01% w/w to about 0.05% w/w, or from about 0.02% w/w to about 0.04% w/w.

In some embodiments, the antioxidant is butylated hydroxyanisole (BHA).

In some embodiments, the concentration of the butylated hydroxyanisole (BHA) ranges from about 0.0005% w/w to about 1% w/w, from about 0.001% w/w to about 0.5% w/w, from about 0.002% w/w to about 0.2% w/w, from about 0.005% w/w to about 0.1% w/w, from about 0.01% w/w to about 0.05% w/w, or from about 0.02% w/w to about 0.04% w/w.

In some embodiments, the antioxidant is DL-Alpha tocopherol (Vitamin E).

In some embodiments, the concentration of the DL-Alpha tocopherol (Vitamin E) ranges from about 0.02% w/w to about 5% w/w, from about 0.05% w/w to about 4% w/w, from about 0.1% w/w to about 3% w/w, from about 0.2% w/w to about 2% w/w, from about 0.3% w/w to about 1.8% w/w, from about 0.5% w/w to about 1.5% w/w, or from 0.05 w/w to 1.5 w/w.

In some embodiments, the concentration of the DL-Alpha tocopherol (Vitamin E) ranges from about 0.005% w/w to about 3% w/w, from about 0.01% w/w to about 2% w/w, from about 0.02% w/w to about 1% w/w, from about 0.05% w/w to about 0.5% w/w, from about 0.08% w/w to about 0.4% w/w, or from about 0.1% w/w to about 0.3% w/w.

In some embodiments, the concentration of the DL-Alpha tocopherol (Vitamin E) ranges from about 0.002% w/w to about 2% w/w, from about 0.005% w/w to about 1% w/w, from about 0.01% w/w to about 0.5% w/w, from about 0.02% w/w to about 0.3% w/w, from about 0.03% w/w to about 0.2% w/w, or from about 0.05% w/w to about 0.15% w/w.

The antioxidants according to the invention are commercially available. Thus, for example DL-alpha-tocopherol (Vitamin E) is available from BASF SE, Ludwigshafen, Germany; Butylated hydroxyanisole (BHA) is available from Sigma Aldrich, St Louis, Mo., USA; and Butylated hydroxytoluene (BHT) is available from Merck KGaA, Darmstadt, Germany.

In some embodiments, the pharmaceutical formulation comprises:
(a) Compound A or a pharmaceutically acceptable salt thereof; and
(b) a solubilizer selected from Caprylocaproyl polyoxyl-8 glycerides (Labrasol ALF), Glycerol Monocaprylocaprate (Capmul MCM), Polyoxyl 35 castor oil (Kolliphor EL), Polysorbate 80 (Tween 80), and mixtures thereof.

In some embodiments, the pharmaceutical formulation comprises:
(a) Compound A; and
(b) a solubilizer selected from Caprylocaproyl polyoxyl-8 glycerides (Labrasol ALF), Glycerol Monocaprylocaprate (Capmul MCM), Polyoxyl 35 castor oil (Kolliphor EL), Polysorbate 80 (Tween 80), and mixtures thereof.

In some embodiments, the pharmaceutical formulation comprises:
(a) Compound A or a pharmaceutically acceptable salt thereof;
(b) a solubilizer selected from Caprylocaproyl polyoxyl-8 glycerides (Labrasol ALF), Glycerol Monocaprylocaprate (Capmul MCM), Polyoxyl 35 castor oil (Kolliphor EL), Polysorbate 80 (Tween 80), and mixtures thereof; and
(c) an antioxidant selected from butylated hydroxytoluene (BHT), butylated hydroxyanisole (BHA), DL-alpha tocopherol (Vitamin E), and mixtures thereof.

In some embodiments, the pharmaceutical formulation comprises:
(a) Compound A;
(b) a solubilizer selected from Caprylocaproyl polyoxyl-8 glycerides (Labrasol ALF), Glycerol Monocaprylocaprate (Capmul MCM) Polyoxyl 35 castor oil (Kolliphor EL), Polysorbate 80 (Tween 80), and mixtures thereof; and
(c) an antioxidant selected from butylated hydroxytoluene (BHT), butylated hydroxyanisole (BHA), DL-alpha tocopherol (Vitamin E), and mixtures thereof.

In some embodiments, the pharmaceutical formulation comprises:
(a) Compound A or a pharmaceutically acceptable salt thereof;
(b) a solubilizer selected from Caprylocaproyl polyoxyl-8 glycerides (Labrasol ALF), Glycerol Monocaprylocaprate (Capmul MCM), Polyoxyl 35 castor oil (Kolliphor EL), Polysorbate 80 (Tween 80), and mixtures thereof;
(c) an emulsifier being Glyceryl Monooleate (Peceol); and
(d) an antioxidant selected from butylated hydroxytoluene (BHT), butylated hydroxyanisole (BHA), DL-alpha tocopherol (Vitamin E), and mixtures thereof.

In some embodiments, the pharmaceutical formulation comprises:
(a) Compound A;
(b) a solubilizer selected from Caprylocaproyl polyoxyl-8 glycerides (Labrasol ALF), Glycerol Monocaprylocaprate (Capmul MCM), Polyoxyl 35 castor oil (Kolliphor EL), Polysorbate 80 (Tween 80), and mixtures thereof;
(c) an emulsifier being Glyceryl Monooleate (Peceol); and
(d) an antioxidant selected from butylated hydroxytoluene (BHT), butylated hydroxyanisole (BHA), DL-alpha tocopherol (Vitamin E), and mixtures thereof.

In some embodiments, the pharmaceutical formulation comprises Compound A, Caprylocaproyl polyoxyl-8 glycerides (Labrasol ALF), and Butylated hydroxytoluene (BHT).

In some embodiments, the pharmaceutical formulation comprises:
(a) Compound A presented at a concentration ranging from about 0.1% w/w to about 50% w/w, from about 0.2% w/w to about 40% w/w, from about 0.3% w/w to about 30% w/w, from about 0.5% w/w to about 20% w/w, from about 0.8% w/w to about 15% w/w, or from about 1% w/w to about 10% w/w;
(b) Caprylocaproyl polyoxyl-8 glycerides (Labrasol ALF) presented at a concentration ranging from about 70% w/w to about 99.9% w/w, from about 75% w/w to about 99.7% w/w, from about 80% w/w to about 99.5% w/w, from about 85% w/w to about 99.2% w/w, or from about 90% w/w to about 99% w/w; and
(c) Butylated hydroxytoluene (BHT) presented at a concentration ranging from about 0.0005% w/w to about 1% w/w, from about 0.001% w/w to about 0.5% w/w, from about 0.002% w/w to about 0.2% w/w, from about 0.005% w/w to about 0.1% w/w, from about 0.01% w/w to about 0.05% w/w, or from about 0.02% w/w to about 0.04% w/w In some embodiments, the pharmaceutical formulation comprises Compound A, Glycerol Monocaprylocaprate (Capmul MCM) Polyoxyl 35 castor oil (Kolliphor EL), and butylated hydroxytoluene (BHT).

In some embodiments, the pharmaceutical formulation comprises:
(a) Compound A presented at a concentration ranging from about 0.1% w/w to about 50% w/w, from about 0.2% w/w to about 40% w/w, from about 0.3% w/w to about 30% w/w, from about 0.5% w/w to about 20% w/w, from about 0.8% w/w to about 15% w/w, or from about 1% w/w to about 10% w/w;
(b1) Glycerol Monocaprylocaprate (Capmul MCM) presented at a concentration ranging from about 50% w/w to about 99% w/w, from about 55% w/w to about 95% w/w, from about 60% w/w to about 90% w/w, from about 65% w/w to about 85% w/w, from about 67% w/w to about 82% w/w, or from about 69% w/w to about 79% w/w;

(b2) Polyoxyl 35 castor oil (Kolliphor EL) presented at a concentration ranging from about 5% w/w to about 40% w/w, from about 8% w/w to about 35% w/w, from about 10% w/w to about 30% w/w, from about 12% w/w to about 27% w/w, or from about 14% w/w to about 24% w/w; and (c) Butylated hydroxytoluene (BHT) presented at a concentration ranging from about 0.0005% w/w to about 1% w/w, from about 0.001% w/w to about 0.5% w/w, from about 0.002% w/w to about 0.2% w/w, from about 0.005% w/w to about 0.1% w/w, from about 0.01% w/w to about 0.05% w/w, or from about 0.02% w/w to about 0.04% w/w.

In some embodiments, the pharmaceutical formulation comprises Compound A, Glycerol Monocaprylocaprate (Capmul MCM), Caprylocaproyl polyoxyl-8 glycerides (Labrasol ALF), and Butylated hydroxyanisole (BHA).

In some embodiments, the pharmaceutical formulation comprises:

(a) Compound A presented at a concentration ranging from about 0.1% w/w to about 50% w/w, from about 0.2% w/w to about 40% w/w, from about 0.3% w/w to about 30% w/w, from about 0.5% w/w to about 20% w/w, from about 0.8% w/w to about 15% w/w, or from about 1% w/w to about 10% w/w;

(b1) Glycerol Monocaprylocaprate (Capmul MCM) presented at a concentration ranging from about 35% w/w to about 95% w/w, from about 40% w/w to about 90% w/w, from about 45% w/w to about 85% w/w, from about 55% w/w to about 80% w/w, from about 60% w/w to about 75% w/w, or from about 62% w/w to about 72% w/w;

(b2) Caprylocaproyl polyoxyl-8 glycerides (Labrasol ALF) presented at a concentration ranging from about 10% w/w to about 50% w/w, from about 15% w/w to about 45% w/w, from about 20% w/w to about 40% w/w, from about 22% w/w to about 37% w/w, or from about 24% w/w to about 34% w/w; and (c) Butylated hydroxyanisole (BHA) presented at a concentration ranging from about 0.0005% w/w to about 1% w/w, from about 0.001% w/w to about 0.5% w/w, from about 0.002% w/w to about 0.2% w/w, from about 0.005% w/w to about 0.1% w/w, from about 0.01% w/w to about 0.05% w/w, or from about 0.02% w/w to about 0.04% w/w.

In some embodiments, the pharmaceutical formulation comprises Compound A, Glycerol Monocaprylocaprate (Capmul MCM), Polysorbate 80 (Tween 80), Glyceryl Monooleate (Peceol), and DL-alpha tocopherol (Vitamin E).

In some embodiments, the pharmaceutical formulation comprises:

(a) Compound A presented at a concentration ranging from about 0.1% w/w to about 50% w/w, from about 0.2% w/w to about 40% w/w, from about 0.3% w/w to about 30% w/w, from about 0.5% w/w to about 20% w/w, from about 0.8% w/w to about 15% w/w, or from about 1% w/w to about 10% w/w;

(b1) Glycerol Monocaprylocaprate (Capmul MCM) presented at a concentration ranging from about 15% w/w to about 70% w/w, from about 20% w/w to about 65% w/w, from about 25% w/w to about 60% w/w, from about 30% w/w to about 55% w/w, from about 35% w/w to about 50% w/w, or from about 37% w/w to about 47% w/w;

(b2) Polysorbate 80 (Tween 80) presented at a concentration ranging from about 3% w/w to about 25% w/w, from about 4% w/w to about 20% w/w, from about 5% w/w to about 17% w/w, from about 6% w/w to about 14% w/w, or from about 7% w/w to about 13% w/w;

(c) Glyceryl Monooleate (Peceol) presented at a concentration ranging from about 15% w/w to about 70% w/w, from about 20% w/w to about 65% w/w, from about 25% w/w to about 60% w/w, from about 30% w/w to about 55% w/w, from about 35% w/w to about 50% w/w, or from about 38% w/w to about 48% w/w; and (d) DL-Alpha tocopherol (Vitamin E) presented at a concentration ranging from about 0.02% w/w to about 5% w/w, from about 0.05% w/w to about 4% w/w, from about 0.1% w/w to about 3% w/w, from about 0.2% w/w to about 2% w/w, from about 0.3% w/w to about 1.8% w/w, or from about 0.5% w/w to about 1.5% w/w.

In some embodiments, the pharmaceutical formulation comprises Compound A, Glycerol Monocaprylocaprate (Capmul MCM), Caprylocaproyl polyoxyl-8 glycerides (Labrasol ALF), Polysorbate 80 (Tween 80), Glyceryl Monooleate (Peceol), and DL-alpha tocopherol (Vitamin E).

In some embodiments, the pharmaceutical formulation comprises:

(a) Compound A presented at a concentration ranging about 0.1% w/w to about 50% w/w, from about 0.2% w/w to about 40% w/w, from about 0.3% w/w to about 30% w/w, from about 0.5% w/w to about 20% w/w, from about 0.8% w/w to about 15% w/w, or from about 1% w/w to about 10% w/w;

(b1) Glycerol Monocaprylocaprate (Capmul MCM) presented at a concentration ranging from about 15% w/w to about 60% w/w, from about 20% w/w to about 65% w/w, from about 20% w/w to about 55% w/w, from about 25% w/w to about 50% w/w, from about 30% w/w to about 45% w/w, or from about 32% w/w to about 42% w/w;

(b2) Caprylocaproyl polyoxyl-8 glycerides (Labrasol ALF) presented at a concentration ranging from about 3% w/w to about 25% w/w, from about 4% w/w to about 20% w/w, from about 5% w/w to about 17% w/w, from about 6% w/w to about 14% w/w, or from about 7% w/w to about 13% w/w;

(b3) Polysorbate 80 (Tween 80) presented at a concentration from about 3% w/w to about 25% w/w, from about 4% w/w to about 20% w/w, from about 5% w/w to about 17% w/w, from about 6% w/w to about 14% w/w, or from about 7% w/w to about 13% w/w;

(c) Glyceryl Monooleate (Peceol) presented at a concentration ranging from about 15% w/w to about 60% w/w, from about 20% w/w to about 65% w/w, from about 20% w/w to about 55% w/w, from about 25% w/w to about 50% w/w, from about 30% w/w to about 45% w/w, or from about 33% w/w to about 43% w/w; and (d) DL-Alpha tocopherol (Vitamin E) presented at a concentration ranging from about 0.02% w/w to about 5% w/w, from about 0.05% w/w to about 4% w/w, from about 0.1% w/w to about 3% w/w, from about 0.2% w/w to about 2% w/w, from about 0.3% w/w to about 1.8% w/w, or from about 0.5% w/w to about 1.5% w/w.

In some embodiments, the pharmaceutical formulation comprises:

(a) Compound A presented at a concentration ranging about 0.1% w/w to about 50% w/w, from about 0.2% w/w to about 40% w/w, from about 0.3% w/w to about 30% w/w, from about 0.5% w/w to about 20% w/w, from about 0.8% w/w to about 15% w/w, or from about 1% w/w to about 10% w/w;

(b1) Glycerol Monocaprylocaprate (Capmul MCM) presented at a concentration ranging from about 15% w/w to about 60% w/w, from about 20% w/w to about 65% w/w, from about 20% w/w to about 55% w/w, from about 25% w/w to about 50% w/w, from about 30% w/w to about 45% w/w, or from about 32% w/w to about 42% w/w;

(b2) Caprylocaproyl polyoxyl-8 glycerides (Labrasol ALF) presented at a concentration ranging from about 3% w/w to about 25% w/w, from about 4% w/w to about 20% w/w, from about 5% w/w to about 17% w/w, from about 6% w/w to about 14% w/w, or from about 7% w/w to about 13% w/w;

(b3) Polysorbate 80 (Tween 80) presented at a concentration from about 3% w/w to about 25% w/w, from about 4% w/w to about 20% w/w, from about 5% w/w to about 17% w/w, from about 6% w/w to about 14% w/w, or from about 7% w/w to about 13% w/w;

(c) Glyceryl Monooleate (Peceol) presented at a concentration ranging from about 15% w/w to about 60% w/w, from about 20% w/w to about 65% w/w, from about 20% w/w to about 55% w/w, from about 25% w/w to about 50% w/w, from about 30% w/w to about 45% w/w, or from about 33% w/w to about 43% w/w; and (d) DL-Alpha tocopherol (Vitamin E) presented at a concentration ranging from about 0.005% w/w to about 3% w/w, from about 0.01% w/w to about 2% w/w, from about 0.02% w/w to about 1% w/w, from about 0.05% w/w to about 0.5% w/w, from about 0.08% w/w to about 0.4% w/w, or from about 0.1% w/w to about 0.3% w/w.

In some embodiments, the pharmaceutical formulation comprises:

(a) Compound A presented at a concentration ranging about 0.1% w/w to about 50% w/w, from about 0.2% w/w to about 40% w/w, from about 0.3% w/w to about 30% w/w, from about 0.5% w/w to about 20% w/w, from about 0.8% w/w to about 15% w/w, or from about 1% w/w to about 10% w/w;

(b1) Glycerol Monocaprylocaprate (Capmul MCM) presented at a concentration ranging from about 15% w/w to about 60% w/w, from about 20% w/w to about 65% w/w, from about 20% w/w to about 55% w/w, from about 25% w/w to about 50% w/w, from about 30% w/w to about 45% w/w, or from about 32% w/w to about 42% w/w;

(b2) Caprylocaproyl polyoxyl-8 glycerides (Labrasol ALF) presented at a concentration ranging from about 3% w/w to about 25% w/w, from about 4% w/w to about 20% w/w, from about 5% w/w to about 17% w/w, from about 6% w/w to about 14% w/w, or from about 7% w/w to about 13% w/w;

(b3) Polysorbate 80 (Tween 80) presented at a concentration from about 3% w/w to about 25% w/w, from about 4% w/w to about 20% w/w, from about 5% w/w to about 17% w/w, from about 6% w/w to about 14% w/w, or from about 7% w/w to about 13% w/w;

(c) Glyceryl Monooleate (Peceol) presented at a concentration ranging from about 15% w/w to about 60% w/w, from about 20% w/w to about 65% w/w, from about 20% w/w to about 55% w/w, from about 25% w/w to about 50% w/w, from about 30% w/w to about 45% w/w, or from about 33% w/w to about 43% w/w; and (d) DL-Alpha tocopherol (Vitamin E) presented at a concentration ranging from about 0.002% w/w to about 2% w/w, from about 0.005% w/w to about 1% w/w, from about 0.01% w/w to about 0.5% w/w, from about 0.02% w/w to about 0.3% w/w, from about 0.03% w/w to about 0.2% w/w, or from about 0.05% w/w to about 0.15% w/w.

In some embodiments, the pharmaceutical formulation comprises:

(a) Compound A from about 1% w/w to about 10% w/w or from about 5% w/w to about 10%;

(b1) Glycerol Monocaprylocaprate (Capmul MCM) presented at a concentration ranging from about 30% w/w to about 40% w/w;

(b2) Caprylocaproyl polyoxyl-8 glycerides (Labrasol ALF) presented at a concentration ranging from about 7% w/w to about 13% w/w;

(b3) Polysorbate 80 (Tween 80) presented at a concentration from about 7% w/w to about 13% w/w;

(c) Glyceryl Monooleate (Peceol) presented at a concentration ranging from about 33% w/w to about 43% w/w; and (d) DL-Alpha tocopherol (Vitamin E) presented at a concentration ranging from about 0.05% w/w to about 1.5% w/w or ranging from 0.5% w/v to 1.0% w/v.

Additional Therapeutic Agents

It is understood that Compound A or a pharmaceutically acceptable salt is used in combination with one or more additional therapeutic agents for treating or preventing a disease or condition disclosed herein.

Thus, in some embodiments, the pharmaceutical formulation of the present disclosure comprises Compound A or a pharmaceutically acceptable salt and the one or more additional therapeutic agents. Alternatively, Compound A or a pharmaceutically acceptable salt and the one or more additional therapeutic agents may be formulated in separated pharmaceutical formulations. In some embodiments, the separated pharmaceutical formulations may be included in a pharmaceutical kit.

Examples of suitable additional therapeutic agents include, but are not limited to, α2-adrenergic agonists and imidazoline receptor agonists such as clonidine; anti-depressants including selective serotonin reuptake inhibitors (SSRIs) such as citalopram, dapoxetine, escitalopram, fluoxetine, fluvoxamine, paroxetine and sertraline, and selective serotonin-norepinephrine reuptake inhibitors (SNRIs) such as desvenlafaxine, duloxetine, levomilnacipran, milnacipran and venlafaxine, and serotonin modulator and stimulators (SMSs) such as vortioxetine and vilazodone, also serotonin-noradrenaline-dopamine reuptake inhibitors such as tesofensine; anti-obesity/weight loss medications including inverse agonists for the cannabinoid receptor CB1 such as rimonabant, and MC4 receptor agonists such as bremelanotide, modimelanotide, PF-00446687, PL-6983, PL-8905, setmelanotide, and drugs that improve glycaemic control such as insulin and long-acting forms of this hormone such as aspart, detemir, glargine, isophane and lispro, and dipeptidyl peptidase-4 (DPP-4) inhibitors such as anagliptin, aloglitin, dutogliptin, linagliptin, omarigliptin, saxagliptin, sitagliptin, teneligliptin, trelagliptin and vildagliptin, and GLP-1 receptor agonists such as albiglutide, dulaglutide, exenatide, liraglutide, lixisenatide and semaglutide, subtype 2 sodium-glucose transport (SGLT-2) inhibitors such as canagliflozin, dapagliflozin, empagliflozin and ipragliflozin, and glycoside hydrolase inhibitors such as acarbose and miglitol, and meglitinides such as repaglinide and nateglinide, and sulfonylureas such as glibenclamide (glyburide), glibornuride, gliclazide, glimepiride, glipizide, gliquidone, glisoxepide and glyclopyramide, and thiazolidinediones such as pioglitazone and rosiglitazone, by also achieving glycaemic control by decreasing hepatic glucose production, decreasing glucose absorption and increasing insulin-mediated glucose uptake such as metformin, and psychostimulants/anticonvulsants such as phentermine/topiramate, and norepinephrine-dopamine reuptake inhibitor (NDRI), nicotinic receptor antagonist/opiate antagonists such as bupropion/naltrexone, and selective serotonin 2c receptor agonists such as lorcaserin, and phosphodiesterase type-4 inhibitors such as apremilast, cilomilast, ibudilast, piclamilast and roflumilast; kappa opioid agonists such as dynorphin analogues, nalfurafine and pentazocine; aromatase inhibitors such as anastrozole, exemestane, letrozole and testolactone; gonadotropin-releasing hormone receptor agonists such as leuprolide, buserelin, histrelin, goserelin, deslorelin, nafarelin and triptorelin; gonadotropin-releasing hormone receptor antagonists such as ASP1707, elagolix, relugolix and linzagolix (OBE2109); and antiandrogens (androgen receptor blockers) such as cyproterone acetate, apalutamide, bicalutamide, darolutamide, enzalutamide, flutamide, nilutamide; CYP17A1 inhibitors such as abiraterone, ketoconazole and seviteronel; and combined androgen receptor blockers and CYP17A1 inhibitors such as galeterone, and hormone replacement therapies such as estrogen-only medications including conjugated estrogens, estradiol, esterified estrogen, estropipate and synthetic conjugated estrogens; progestin-only medications including micronized progesterone and medroxyprogesterone acetate; combination estrogen and progestin medicines including estradiol/norethindrone acetate, estradiol/drospirenone, estradiol/levonorgestrel, ethinyl estradiol/norethindrone acetate, estradiol/norgestimate, conjugated estrogen/medroxyprogesterone; combination estrogen and SERMS including conjugated estrogen/bazedoxifene; selective estrogen receptor modulators (SERMs) such as bazedoxifene, clomifene, cyclofenil, tamoxifen, ormeloxifene, toremifene, raloxifene, lasofoxifene and ospemifene; selective estrogen receptor degraders (SERDs) such as fulvestrant, brilanestrant and elacestrant.

In some embodiments, the one or more additional therapeutic agents is selected from aromatase inhibitors such as anastrozole, exemestane, letrozole and testolactone; selective estrogen receptor modulators (SERMs) such as bazedoxifene, clomifene, cyclofenil, tamoxifen, ormeloxifene, ospemifene, toremifene, raloxifene and lasofoxifene; selective estrogen receptor degraders (SERDs) such as fulvestrant, brilanestrant and elacestrant.

In some embodiments, the one or more additional therapeutic agents is selected from drugs that improve glycaemic control such as insulin and long-acting forms of this hormone such as aspart, detemir, glargine, isophane and lispro, and dipeptidyl peptidase-4 (DPP-4) inhibitors such as anagliptin, aloglitin, dutogliptin, linagliptin, omarigliptin, saxagliptin, sitagliptin, teneligliptin, trelagliptin and vildagliptin, and GLP-1 receptor agonists such as albiglutide, dulaglutide, exenatide, liraglutide, lixisenatide and semaglutide; subtype 2 sodium-glucose transport (SGLT-2) inhibitors such as canagliflozin, dapagliflozin, empagliflozin and ipragliflozin, and glycoside hydrolase inhibitors such as acarbose and miglitol, and meglitinides such as repaglinide and nateglinide, and sulfonylureas such as glibenclamide (glyburide), glibornuride, gliclazide, glimepiride, glipizide, gliquidone, glisoxepide and glyclopyramide, and thiazolidinediones such as pioglitazone and rosiglitazone, by also achieving glycaemic control by decreasing hepatic glucose production, decreasing glucose absorption and increasing insulin-mediated glucose uptake such as metformin.

In some embodiments, the one or more additional therapeutic agents is selected from drugs that improve glycaemic control such as insulin and long-acting forms of this hormone such as aspart, detemir, glargine, isophane and lispro, and Dipeptidyl peptidase-4 (DPP-4) inhibitors such as anagliptin, aloglitin, dutogliptin, linagliptin, omarigliptin, saxagliptin, sitagliptin, teneligliptin, trelagliptin and vildagliptin, and GLP-1 receptor agonists such as albiglutide, dulaglutide, exenatide, liraglutide, lixisenatide and semaglutide; and Subtype 2 sodium-glucose transport (SGLT-2) inhibitors such as canagliflozin, dapagliflozin, empagliflozin and ipragliflozin; and Sulfonylureas such as glibenclamide (glyburide), glibornuride, gliclazide, glimepiride, glipizide, gliquidone, glisoxepide and glyclopyramide, and and increasing insulin-mediated glucose uptake such as metformin.

Other Aspects of the Formulation

It is understood that the pharmaceutical formulation of the present disclosure may be formulated for enteral/gastrointestinal administration, parenteral administration, or topical administration. In some embodiments, the pharmaceutical formulation of the present disclosure is formulated for oral administration (i.e., oral pharmaceutical formulation).

The pharmaceutical compositions for oral administration according to the present invention may be solid, liquid or semi-solid at ambient temperatures, but preferably are presented as liquids. Particularly preferred compositions of the present invention are liquid oral unit dosage forms, more preferably filled soft capsules, e.g. gelatin capsules.

In some embodiments, the pharmaceutical formulation of the present invention may be made using methods and techniques that are commonly employed in preparing such preparations within the pharmaceutical industry.

In some embodiments, the pharmaceutical formulation of the present invention may be prepared in conventional manner, for example, by appropriate mixing of the ingredients in one or more vessels, the ingredients being dissolved using established pharmaceutical techniques.

In a typical procedure for the preparation of the pharmaceutical formulation according to the present invention, the active ingredient is dissolved in the mixture of the excipients maintaining the temperature at 30° C.-40° C. under an inert atmosphere eg nitrogen gas blanket, and under yellow light or protected from light, until the active ingredient is completely solubilised and then stored in the sealed containers until further use.

The active ingredient is selected from Compound A or a pharmaceutically acceptable salt thereof, or Compound A as anhydrous crystalline form (Form 1) or the active ingredient is Compound A or a pharmaceutically acceptable salt thereof, or Compound A as anhydrous crystalline form (Form 1) with one or more additional therapeutic agents.

Thus, the present invention also provides a method for preparing the pharmaceutical formulations according to the present invention by dissolving the active ingredient into at least of one excipient.

In some embodiments, the active ingredient is Compound A or a pharmaceutically acceptable salt thereof. In some embodiments, the active ingredient is Compound A.

In some embodiments, the active ingredient is Compound A as anhydrous crystalline form (Form 1).

In some embodiments, the active ingredient is Compound A or a pharmaceutically acceptable salt thereof, or Compound A as anhydrous crystalline form (Form 1) with one or more additional therapeutic agents.

It is understood that, where the formulations of the invention are presented as soft gelatin capsules, the capsule shell may suitably be made of gelatins such as Gelatin, NF, EP and may include plasticizers such as anidrisorb, glycerin or sorbitol, water, preservatives, colorants(s), and opacifying agent(s) such as titanium dioxide.

The capsule may be of any shape, suitably the capsules may be elongated such as ellipsoidal, oblong, oval or cylindrical with rounded ends. In some embodiments, the capsule contains from about 1 mg to about 500 mg, from about 1 mg to about 250 mg, from about 1 mg to about 100 mg, from about 2 mg to about 50 mg, from about 3 mg to about 40 mg, from about 4 mg to about 30 mg, or from about 5 mg to about 29 mg of Compound A. In some embodiments, the capsule contains about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, or about 29 mg of Compound A.

It is understood that the required amount of Compound A in the pharmaceutical formulation of the present disclosure will depend upon a number of factors including the severity of the condition to be treated and the age and condition of the recipient and will ultimately be at the discretion of the attendant physician.

The soft gelatin capsule may contain different proportions of gelatin, glycerine, sorbitol sorbitan solution, and water.

It is understood that the soft gelatin capsule may be prepared by methods and techniques that are known to a skilled artisan. For example, the soft gelatin capsule may be prepared by the rotary-die encapsulation process.

The rotary die process involves the continuous formation of a heat seal between two ribbons of gelatin, simultaneous with dosing of the fill liquid into each capsule. (J. P. Stanley, *The Theory and Practice of Industrial Pharmacy*, 3$^{rd}$ Ed., 1986, p 398-412).

Specifically, during the encapsulation process, the gelatin receiver is stationed above the encapsulation machine. The converted gelatin mass is gravity fed through two heated gelatin hoses into heated gelatin spreader boxes. At the end of each gelatin hose is a modulator valve. The modulator valve is equipped with a diaphragm that is connected to compressed air. A 100-micron mesh filter bag is attached at the end of the modulator value filtering any particulates from the gel mass. The level of the gelatin within the spreader box activates a proximity switch allowing the compressed air to close the diaphragm within the modulator valve, thereby stopping the flow of the gelatin mass. Once the level of gelatin in the box is reduced, the compressed air is deactivated allowing the gelatin to flow through the modulator valve. The spreader boxes are mounted above the casting drum on each side of the encapsulation machine and are secured by mounting brackets. The spreader box spreads the gelatin mass onto the casting drum evenly at the desired thickness.

The encapsulation machine casts a thin ribbon of molten gelatin onto a water-cooled, circular casting drum that rotates at a speed directly proportional to the machine/die speed. The gelatin ribbon is cooled on the casting drum, then pulled off and threaded through a series of sparge tubes, which lubricate the inside and outside of the gelatin ribbon. Immediately after the gelatin ribbon is lubricated, it passes through the inline print unit, which applies the print logo to the ribbon. Next, the gelatin ribbon is threaded through the encapsulation machine between the wedge and the rotary dies. The wedge is positioned on top of the gelatin ribbon and the rotary dies. The wedge is utilized to heat the gelatin ribbon before the rotary dies cut the soft gelatin shell halves. The heat from the wedge is utilized to facilitate the sealing of the two soft gelatin shell halves. Additionally, the wedge is employed in the filling of the soft geltin capsules, via the positive displacement medicine pump, which doses the fill material through the wedge into the forming soft gelatin capsules.

Before starting encapsulation, several start-up in process checks are performed. Once all parameters are within the acceptable range as per the Master Batch Record, encapsulation process is initiated. In-process checks are performed at regular intervals during encapsulation to examine process responses and the results are documented. The electronic data system automatically records the sample collecting time, in process results, and any deviations or production events during encapsulation. The in-process checks include: fill weight, shell weight, and seal thickness (leading and trailing seals). Visual checks are performed at the machine, including soft gelatin shape and print quality during the encapsulation process. The soft gelatin shell weights are measured and recorded at the same time the fill weights are measured. Fill and shell weights are recorded at regular intervals with seal thickness checks (leading and trailing seals). After encapsulation, the soft gelatin capsules are tumbled until they can be spread onto shallow trays to enable capsules to cool and lose water. The shallow trays with soft gelatin capsules are then dried in a drying tunnel at controlled humidity and temperature to reduce the shell moisture content to inhibit growth of mold and bacteria, prevent capsules from sticking together, and provide capsule rigidity and consistent shape. The drying endpoint is typically determined through hardness testing. Upon reaching a nominal hardness target, soft gelatin capsules are then transferred from shallow trays into deep trays after release from drying for bulk packing.

Commercial manufacturing follows the same process but on a much larger scale. Timelines for production of a single batch of ~1,000,000 soft gelatin capsulescould range from 4-5 days up to 14+ days, depending primarily on the capsule drying time stage.

Thus, the present invention provides a method for producing a soft gelatin capsule comprising the steps of providing a capsule shell, mixing a formulation comprising Compound A or pharmaceutically acceptable salts thereof and at least one excipient, and incorporating the formulation into the capsule shell.

In some embodiments, the formulation comprises Compound A.

In some embodiments, the formulation is a liquid formulation. In some embodiment, the formulation is liquid and comprises Compound A.

Methods of Use

In some aspects, the present disclosure provides a method of treating or preventing a disease or condition, comprising administering to a subject in need thereof a pharmaceutically effective amount of Compound A or a pharmaceutically acceptable salt thereof.

In some aspects, the present disclosure provides a method of treating or preventing a disease or condition, comprising administering to a subject in need thereof a pharmaceutically effective amount of a pharmaceutical formulation disclosed herein.

In some embodiments, Compound A or the pharmaceutical formulation disclosed herein is administered once daily.

In some embodiments, Compound A or the pharmaceutical formulation disclosed herein is administered two or more times daily (e.g., two, three, four, five, six, sevel, eight, nine, or ten or more times daily).

In some embodiments, the disease is a sex-hormone dependent disease.

In some embodiments, the sex hormone-dependent diseases are selected from endometriosis, uterine fibrosis, heavy menstrual bleeding, polycystic ovary syndrome (PCOS) and hot flushes.

In some embodiments, the disease is hot flushes. In some embodiments, the disease is a weight-related disease.

In some aspects, the present invention provides a method of treating or preventing a sex hormone-dependent disease, comprising administering to a subject in need thereof a pharmaceutically effective amount of a pharmaceutical formulation disclosed herein.

In some aspects, the present invention provides a method of treating or preventing a sex hormone-dependent disease, selected from endometriosis, uterine fibrosis, heavy menstrual bleeding, polycystic ovary syndrome (PCOS) or hot flushes, comprising administering to a subject in need thereof a pharmaceutically effective amount of a pharmaceutical formulation disclosed herein.

In some aspects, the present invention provides a method of treating or preventing hot flushes, comprising administering to a subject in need thereof a pharmaceutically effective amount of a pharmaceutical formulation disclosed herein.

In some embodiments, the disease is a leptin-related disease.

In some embodiments, the disease is a disorder of pregnancy.

In some aspects, the present disclosure provides a method of treating or preventing a leptin-related disease, comprising administering to a subject in need thereof a pharmaceutically effective amount of Compound A or a pharmaceutically acceptable salt thereof.

In some aspects, the present disclosure provides a method of treating or preventing a disorder of pregnancy, comprising administering to a subject in need thereof a pharmaceutically effective amount of Compound A or a pharmaceutically acceptable salt thereof.

In some embodiments, the symptoms of the perimenopause, the menopause, or the post menopause are selected from a pathological gain of excess body fat and/or excess body weight, insomnia, sleep disturbances and night-time awakenings, anxiety and depression, urinary symptoms of urgency and dysuria.

In some aspects, the present disclosure provides a method of treating or preventing symptoms of the perimenopause, the menopause, or the post menopause selected from a pathological gain of excess body fat and/or excess body weight, insomnia, sleep disturbances and night-time awakenings, anxiety and depression, urinary symptoms of urgency and dysuria, comprising administering to a subject in need thereof a pharmaceutically effective amount of Compound A or a pharmaceutically acceptable salt thereof.

In some aspects, the present invention provides a method of treating or preventing the symptoms associated with the andropause are selected from a pathological gain of excess body fat and/or excess body weight, insomnia, sleep disturbances, night-time awakenings, anxiety and depression, urinary symptoms of urgency and dysuria, comprising administering to a subject in need thereof a pharmaceutically effective amount of Compound A or a pharmaceutically acceptable salt thereof.

In some embodiments, Compound A or a pharmaceutically acceptable salt thereof is administered at a daily dosage ranging from about 1 mg to about 500 mg, from about 1 mg to about 250 mg, from about 1 mg to about 100 mg, from about 2 mg to about 50 mg, from about 3 mg to about 40 mg, from about 4 mg to about 30 mg, or from about 5 mg to about 29 mg.

In some embodiments, Compound A or a pharmaceutically acceptable salt thereof is administered at a daily dosage being about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, or about 29 mg.

In some embodiments the daily dosage of Compound A or a pharmaceutically acceptable salt thereof ranges from 25 mg to 160 mg/day. Particularly, 25 mg, 40 mg, 60 mg, 80 mg, 100 mg, 120 mg and 160 mg/day.

In some embodiments, the method further comprises administering to the subject in need thereof one or more additional therapeutic agents.

In some embodiments, Compound A or the pharmaceutically acceptable salt thereof and the one or more additional therapeutic agents are administered simultaneously.

In some embodiments, Compound A or the pharmaceutically acceptable salt thereof and the one or more additional therapeutic agents are administered in a single pharmaceutical formulation.

In some embodiments, Compound A or the pharmaceutically acceptable salt thereof and the one or more additional therapeutic agents are administered in separate pharmaceutical formulations.

In some embodiments, Compound A or the pharmaceutically acceptable salt thereof and the one or more additional therapeutic agents are administered are administered in temporal proximity.

In some embodiments, Compound A or the pharmaceutically acceptable salt thereof and the one or more additional therapeutic agents are administered are administered sequentially in either order or in alternation.

In some embodiments, Compound A or the pharmaceutically acceptable salt thereof is administered prior to the administration of the one or more additional therapeutic agents.

In some embodiments, the one or more additional therapeutic agents is administered prior to the administration of Compound A or the pharmaceutically acceptable salt thereof.

In some embodiments, the pharmaceutical formulation and the one or more additional therapeutic agents are administered simultaneously.

In some embodiments, the pharmaceutical formulation and the one or more additional therapeutic agents are administered are administered in temporal proximity.

In some embodiments, the pharmaceutical formulation and the one or more additional therapeutic agents are administered are administered sequentially in either order or in alternation.

In some embodiments, the pharmaceutical formulation is administered prior to the administration of the one or more additional therapeutic agents.

In some embodiments, the one or more additional therapeutic agents is administered prior to the administration of the pharmaceutical formulation.

In some aspects, the present disclosure provides a pharmaceutical formulation disclosed herein for use in the treatment or prevention of a disease or a condition disclosed herein.

In some aspects, the present invention provides a pharmaceutical formulation disclosed herein, for use in the treatment or prevention of a sex hormone-dependent disease.

In some aspects, the present invention provides a pharmaceutical formulation disclosed herein, for use in the treatment or prevention of a sex hormone-dependent disease selected from endometriosis, uterine fibrosis, heavy menstrual bleeding, polycystic ovary syndrome (PCOS) and hot flushes.

In some aspects, the present invention provides a pharmaceutical formulation disclosed herein, for use in the treatment or prevention of hot flushes.

In some aspects, the present disclosure provides a pharmaceutical formulation disclosed herein for use in combination with one or more additional therapeutic agents in the treatment or prevention of a disease or a condition disclosed herein.

In some aspects, the present disclosure provides a combination of a pharmaceutical formulation disclosed herein and one or more additional therapeutic agents for use in the treatment or prevention of a disease or a condition disclosed herein.

In some aspects, the present disclosure provides use of a pharmaceutical formulation disclosed herein in the manufacture of a medicatment for treating or preventing a disease or a condition disclosed herein.

In some aspects, the present invention provides use of a pharmaceutical formulation disclosed herein in the manufacture of a medicatment for treating or preventing a sex hormone-dependent disease. In some aspects, the present invention provides use of a pharmaceutical formulation disclosed herein in the manufacture of a medicatment for treating or preventing a sex hormone-dependent disease selected from endometriosis, uterine fibrosis, heavy menstrual bleeding, polycystic ovary syndrome (PCOS) and hot flushes.

In some aspects, the present invention provides use of a pharmaceutical formulation disclosed herein in the manufacture of a medicatment for treating or preventing hot flushes.

In some aspects, the present disclosure provides use of a pharmaceutical formulation disclosed herein in combination with one or more additional therapeutic agents in the manufacture of a medicatment for treating or preventing a disease or a condition disclosed herein.

In some aspects, the present disclosure provides use of the combination of a pharmaceutical formulation disclosed herein and one or more additional therapeutic agents in the manufacture of a medicatment for treating or preventing a disease or a condition disclosed herein.

In some aspects, the present invention provides a use of Compound A or a pharmaceutically acceptable salt thereof in the manufacture of a medicatment for treating or preventing a disease or a condition disclosed herein.

In some aspects, the present invention provides a use of Compound A or a pharmaceutically acceptable salt thereof in the manufacture of a medicatment for treating or preventing a leptin-related disease.

In some aspects, the present invention provides a use of Compound A or a pharmaceutically acceptable salt thereof in the manufacture of a medicatment for treating or preventing a disorder of pregnancy.

In some aspects, the present disclosure provides a use of Compound A or a pharmaceutically acceptable salt thereof in the manufacture of a medicatment of treating or preventing symptoms of the perimenopause, the menopause, or the post menopause selected from a pathological gain of excess body fat and/or excess body weight, insomnia, sleep disturbances and night-time awakenings, anxiety and depression, urinary symptoms of urgency and dysuria.

In some aspects, the present invention provides use of Compound A or a pharmaceutically acceptable salt thereof in the manufacture of a medicatment of treating or preventing the symptoms associated with the andropause selected from a pathological gain of excess body fat and/or excess body weight, insomnia, sleep disturbances, night-time awakenings, anxiety and depression, urinary symptoms of urgency and dysuria.

In some aspects, the present invention provides use of Compound A or a pharmaceutically acceptable salt thereof in combination with one or more additional therapeutic agents in the manufacture of a medicatment for treating or preventing a disease or a condition disclosed herein.

In some aspects, the present invention provides a Compound A or a pharmaceutically acceptable salt thereof in the treatment or prevention of a disease or a condition disclosed herein.

In some aspects, the present invention provides Compound A or a pharmaceutically acceptable salt thereof, for use in the treatment or prevention of a leptin-related disease.

In some aspects, the present invention provides Compound A or a pharmaceutically acceptable salt thereof, for use in the treatment or prevention of a disorder of pregnancy.

In some aspects, the present invention provides Compound A or a pharmaceutically acceptable salt thereof for use in the treatment or prevention of symptoms of the perimenopause, the menopause, or the post menopause selected from a pathological gain of excess body fat and/or excess body weight, insomnia, sleep disturbances and night-time awakenings, anxiety and depression, urinary symptoms of urgency and dysuria.

In some aspects, the present invention provides Compound A or a pharmaceutically acceptable salt thereof for use in the treatment or prevention of the symptoms associated with the andropause selected from a pathological gain of excess body fat and/or excess body weight, insomnia, sleep disturbances, night-time awakenings, anxiety and depression, urinary symptoms of urgency and dysuria.

In some aspects, the present invention provides Compound A or a pharmaceutically acceptable salt thereof in combination with one or more additional therapeutic agents for use in the treatment or prevention of a disease or a condition disclosed herein.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

Other features and advantages of the invention will be apparent from the following detailed description and claims.

EXAMPLES

List of the Abbreviations Used:

NF=National Formulary; EP=European Pharmacopoeia; JP=Japanese Pharmacopoeia; USP—United States Pharmacopeia

Example 1

1.1 Composition

| Fill Material | Amount (mg) | % w/w |
|---|---|---|
| Compound A (Form 1) | 25.00 | 5.00 |
| Glycerol Monocaprylocaprate (Capmul MCM) | 185.25 | 37.05 |
| Caprylocaproyl polyoxyl-8 glycerides (Labrasol ALF) | 47.50 | 9.50 |
| Polysorbate 80 (Tween 80) | 47.50 | 9.50 |
| Glyceryl Monooleate-Peceol | 190.00 | 38.00 |
| DL-Alpha tocopherol (Vitamin E) | 4.75 | 0.95 |
| Total | 500 | 100 |

1.2 Method of Preparation 118.75 grams of Labrasol ALF (pharmacopoeial grade), 118.75 grams of Tween 80 (Polysorbate 80) (pharmacopoeial grade), and 475.00 grams of Peceol (glyceryl monooleate, NF, EP) were weighted in separate stainless steel containers. Peceol was placed into oven at 55° C. (range 50-60° C.) until ready for use. Under an inert atmosphere maintained by nitrogen purging, 62.5 grams of Compound A (free base crystalline form 1) was weighed out inside of an isolator directly into a separate stainless container protected from light by using yellow lighting and then covered with foil or lid and set aside in isolator. Tween 80, EP, NF, JP and Peceol NF, EP were transferred into a Becomix 2.5 L under a steady flow of nitrogen. Under constant nitrogen purge, 463.125 grams of Capmul MCM, EP, and 11.875 grams DL-alpha tocopherol (Vitamin E), USP were weighed inside of isolator directly into separate stainless containers under yellow light and then covered with foil or lid and set aside in isolator. Both materials were combined and mixed by hand with a spatula. The container with Vitamin E, USP was rinsed three times with Capmul MCM, EP to ensure complete transfer of this antioxidant Inside of the isolator (under nitrogen purge), Compound A, as anhydrous crystalline form (Form 1), was added to mixture of Capmul MCM, EP and Vitamin E, USP slowly while mixing. Once the entire dispensed Compound A was transferred, it was mixed via an overhead laboratory mixer with a sawtooth blade for not less than 15 minutes from the time transfer is completed and until adequately dispersed and wetted. The mixture containing Compound A was then transferred into the Becomix 2.5 L under a steady flow of nitrogen. Labrasol ALF (NF, EP) was used to rinse the container used for the Compound A mixture (not less than 3 times) to ensure complete transfer. The nitrogen flow was then turned off and vacuum was applied to the mixture. The mixture was mixed for not less than 60 minutes until all Compound A was visually dissolved, maintaining a temperature at 30° C.-40° C. The final product was de-aerated under vacuum for not less than 30 minutes and then stored in a sealed container (protected from light) under an inert nitrogen blanket until further use.

Similarly to Example 1 the following compositions (Examples 1.a-d and 2-7) were prepared.

Example 1a

| Fill Material | Amount (mg) | % w/w |
|---|---|---|
| Compound A (Form 1) | 40.0 | 5.00 |
| Glycerol Monocaprylocaprate (Capmul MCM) | 296.4 | 37.05 |
| Caprylocaproyl polyoxyl-8 glycerides (Labrasol ALF) | 76.0 | 9.50 |
| Polysorbate 80 (Tween 80) | 76.0 | 9.50 |
| Glyceryl Monooleate (Peceol) | 304.0 | 38.00 |
| DL-Alpha tocopherol (Vitamin E) | 7.6 | 0.95 |
| Total | 800 | 100 |

Example 1b

| Fill Material | Amount (mg) | % w/w |
|---|---|---|
| Compound A (Form 1) | 60 | 6.28 |
| Glycerol Monocaprylocaprate (Capmul MCM) | 351 | 36.7 |
| Caprylocaproyl polyoxyl-8 glycerides (Labrasol ALF) | 90 | 9.4 |
| Polysorbate 80 (Tween 80) | 90 | 9.4 |
| Glyceryl Monooleate (Peceol) | 360 | 37.7 |
| DL-Alpha tocopherol (Vitamin E) | 5 | 0.52 |
| Total | 956 | 100 |

Example 1c

| Fill Material | Amount (mg) | % w/w |
|---|---|---|
| Compound A (Form 1) | 10.0 | 6.25 |
| Glycerol Monocaprylocaprate (Capmul MCM) | 58.5 | 36.6 |
| Caprylocaproyl polyoxyl-8 glycerides (Labrasol ALF) | 15.0 | 9.4 |
| Polysorbate 80 (Tween 80) | 15.0 | 9.4 |
| Glyceryl Monooleate (Peceol) | 60.0 | 37.5 |
| DL-Alpha tocopherol (Vitamin E) | 1.5 | 0.94 |
| Total | 160 | 100 |

Example 1d

| Fill Material | Amount (mg) | % w/w |
|---|---|---|
| Compound A (Form 1) | 25.00 | 5.05 |
| Glycerol Monocaprylocaprate (Capmul MCM) | 185.25 | 37.4 |
| Caprylocaproyl polyoxyl-8 glycerides (Labrasol ALF) | 47.50 | 9.6 |
| Polysorbate 80 (Tween 80) | 47.50 | 9.6 |
| Glyceryl Monooleate (Peceol) | 190.00 | 38.4 |
| Total | 495.25 | 100 |

Example 2

| Fill Material | Amount (mg) | % w/w |
|---|---|---|
| Compound A (Form 1) | 25.00 | 5.00 |
| Caprylocaproyl polyoxyl-8 glycerides (Labrasol ALF) | 474.85 | 94.97 |
| Butylated hydroxytoluene (BHT) | 0.15 | 0.03 |
| Total | 500 | 100 |

Example 3

| Fill Material | Amount (mg) | % w/w |
|---|---|---|
| Compound A (Form 1) | 25.00 | 5.00 |
| Glycerol Monocaprylocaprate (Capmul MCM) | 379.85 | 75.97 |
| Polyoxyl 35 castor oil (Kolliphor EL) | 95.00 | 19.00 |
| Butylated hydroxytoluene (BHT) | 0.15 | 0.03 |
| Total | 500 | 100 |

Example 4

| Fill Material | Amount (mg) | % w/w |
|---|---|---|
| Compound A (Form 1) | 25.00 | 5.00 |
| Caprylocaproyl polyoxyl-8 glycerides (Labrasol ALF) | 142.35 | 28.47 |
| Glycerol Monocaprylocaprate (Capmul MCM) | 332.50 | 66.50 |
| Butylated hydroxyanisole (BHA) | 0.15 | 0.03 |
| Total | 500 | 100 |

Example 5

| Fill Material | Amount (mg) | % w/w |
|---|---|---|
| Compound A (Form 1) | 25.00 | 5.00 |
| Glycerol Monocaprylocaprate - (Capmul MCM) | 209.00 | 41.80 |
| Polysorbate 80 (Tween 80) | 47.50 | 9.50 |
| Glyceryl Monooleate (Peceol) | 213.75 | 42.75 |
| DL-Alpha tocopherol (Vitamin E) | 4.75 | 0.95 |
| Total | 500 | 100 |

Example 6

| Fill Material | Amount (mg) | % w/w |
|---|---|---|
| Compound A (Form 1) | 25.00 | 5.04 |
| Glycerol Monocaprylocaprate - (Capmul MCM) | 185.25 | 37.34 |
| Caprylocaproyl polyoxyl-8 glycerides (Labrasol ALF) | 47.50 | 9.57 |
| Polysorbate 80 (Tween 80) | 47.50 | 9.57 |
| Glyceryl Monooleate (Peceol) | 190.00 | 38.29 |
| DL-Alpha tocopherol (Vitamin E) | 0.90 | 0.18 |
| Total | 496.15 | 100 |

Example 7

| Fill Material | Amount (mg) | % w/w |
|---|---|---|
| Compound A (Form 1) | 25.00 | 5.04 |
| Glycerol Monocaprylocaprate (Capmul MCM) | 185.25 | 37.34 |
| Caprylocaproyl polyoxyl-8 glycerides (Labrasol ALF) | 47.50 | 9.57 |
| Polysorbate 80 (Tween 80) | 47.50 | 9.57 |
| Glyceryl Monooleate (Peceol) | 190.00 | 38.29 |
| DL-alpha tocopherol (Vitamin E) | 0.45 | 0.091 |
| Total | 495.70 | 100 |

Example 7a

The formulations from Examples 1, to 7 were encapsulated using a commercially available rotary-die process to produce soft gelatin capsules. Commercially available gelatin capsules were used.

Example 8. Comparative Oral PK Study Female Cynomolgus Monkeys

The comparative PK of Compound A after oral administration to female cynomolgus monkeys of current hard gelatin capsules (50 mg/capsule) and soft gelatin capsules containing the composition described in Example 1 (25 mg/capsule) was assessed.

The composition of hard gelatin capsules (50 mg/capsule) is provided in Table 3 of this specification.

Study Protocol

Six female cynomolgus monkeys were placed into two groups of three animals per group. Overnight fasting (targeted between 8-10 hours) was required before dosing, and food was targeted to be returned four hours post-dosing. Water was provided ad libitum.

On Day 1, for Group 1, the desired amount of Compound A in hard gelatin capsule was dispensed at a dose level of 50 mg/animal (capsule/animal) for oral administration.

For Group 2 the desired amount of Example 1 in soft gelatin capsule soft gelatin capsule was dispensed at a dose level of 25 mg/animal (capsule/animal) for oral administration.

On Day 8, for Group 1, the desired amount of Example 1 in soft gelatin capsule was dispensed at a dose level of 25 mg/animal (capsule/animal) for oral administration.

For Group 2 the desired amount of Compound A in hard gelatin capsule was dispensed at a dose level of 50 mg/animal (capsule/animal) for oral administration.

Blood samples were collected on Day 1 and Day 8 before starting the treatment then 0.5, 1, 2, 3, 4, 8, 12, 24, and 48 hours after the treatment.

Results

Figure 2:
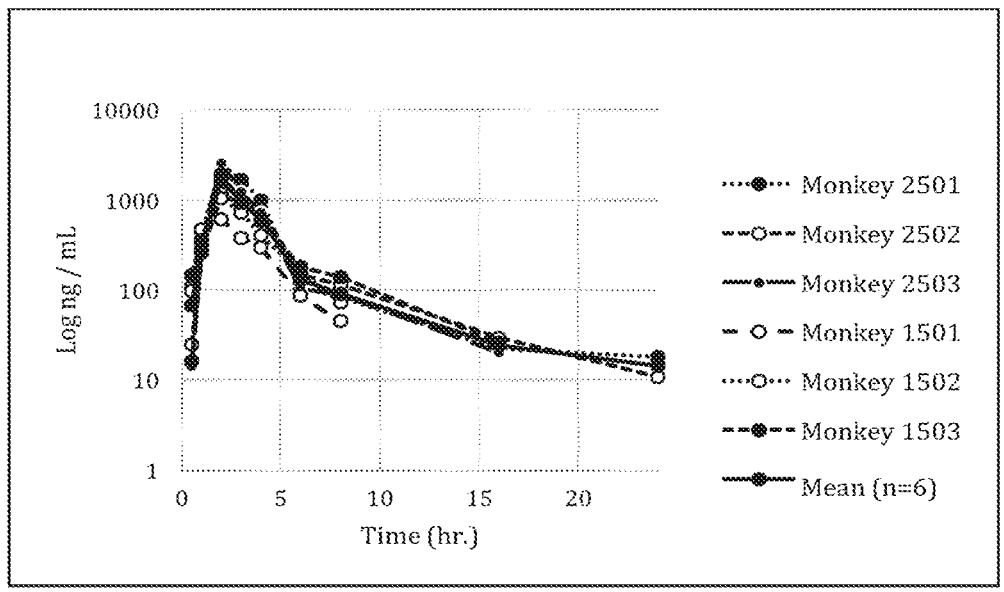
FIG. 2 provides PK plots for individual animals and means for the soft gelatin liquid formulation of Compound A.

PK profiles of Compound A from the six female cynomolgus monkeys for the hard gelatin capsules and soft gelatin capsules are shown in FIGS. 1 and 2 respectively. As can be seen from the figures, Compound A absorption was rapid with a tmax of 2 h for the soft gelatin capsule formulation and slightly slower and more variable for the hard gelatin capsule formulation (tmax=3.7±2.4 h). Cmax and $AUC_{0-x}$ exposure ratios using the hard gelatin capsule data as reference are shown in Table 4. A surprising decrease in PK variability associated with the soft gelatin capsule administration was observed, as shown by the significant improvement in the Coefficient of Variation % (CV %)s for AUC and Cmax parameters for the soft gelatin capsules compared to the hard gelatin capsules in the study. The CV % for the soft gelatin capsules were 37.8% and 49.2% for the AUC and Cmax respectively, compared with CV % s in excess of 210% for both these parameters with the hard gelatin formulation. The reduced variability of Compound A formulated in the soft gelatin capsule is also very apparent when FIGS. 1 and 2 are compared.

TABLE 4

Dose normalised Cmax and AUC values after a single 25 mg dose in monkeys for Compound A new soft gelatin capsule formulation according to the invention as compared with 50 mg Compound A current hard gelatin capsule formulation.

|  | $AUC_{0-x}$/dose (ng · hr/mL/mg) | | Cmax/dose (ng/mL/mg) | |
| --- | --- | --- | --- | --- |
|  | Hard Gelatin Capsule | Soft Gelatin Capsule | Hard Gelatin Capsule | Soft Gelatin Capsule |
| Mean^ | 45.27 | 174.88 | 11.68 | 65.54 |
| CV % | 210.84 | 37.81 | 217.17 | 49.20 |

^Data shown are dose-normalised values to account for the different doses used with the two formulations Example 9. Comparative Oral PK Study in Healthy Human Post-Menopausal Women The comparative PK of Compound A after oral administration to healthy human post-menopausal women as the current hard gelatin capsules (50 mg Compound A/capsule) and new formulation soft gelatin capsules containing the composition described in Example 1 (25 mg/capsule) was assessed in a Phase 1, open label, randomised, crossover study. The composition of hard gelatin capsules (50 mg/capsule) is provided in Table 3 of this specification.

Study Protocol

Thirty-six healthy human post-menopausal women volunteers each received the formulations of Compound A as a single dose in treatment Periods 1 and 2. The sequence of Periods 1 and 2 was randomised.

Period 1: 100 mg Compound A hard gelatin capsules (as 2×50 mg capsules) OR 25 mg soft gelatin capsule administered after an overnight fast Period 2: 100 mg Compound A hard gelatin capsules (as 2×50 mg capsules) OR 25 mg soft gelatin capsule administered after an overnight fast (whichever they did not receive in Period 1)

Single doses of Compound A were administered to the subjects on the mornings of Day 1 (Period 1) and Day 8 (Period 2). During both periods blood was sampled for assay of Compound A prior to dosing and for up to 72 hours post dose.

Results

For both the 25 mg soft gelatin and 100 mg hard gelatin capsules, mean plasma Compound A concentrations increased rapidly, with median tmax at 1 hour post-dose for the soft gelatin formulation and 1.5 hours post-dose for the hard gelatin. Cmax and $AUC_{0-24}$ exposure PK data for both formulations are shown in Table 5.

TABLE 5

Cmax and AUC values for Compound A new soft gelatin capsule formulation according to the invention as compared with 100 mg Compound A in the current hard gelatin capsule formulation.

| Development Form | | Anhydrous crystalline form (Form1) | |
| --- | --- | --- | --- |
| Formulation | | Hard gelatin capsule | Soft gelatin capsule |
| Study population | | Post-menopausal females | |
| Dose Administered | | 100 mg | 25 mg |
| | N | 36 | 36 |
| $AUC_{0-24}$ | Geometric mean (ng · hr/mL) | 2931 | 786 |
| | CV % | 64.7 | 42.1 |
| Cmax | Geometric mean (ng/mL) | 997 | 332 |
| | CV % | 69.3 | 43.1 |

The data shows that the noteworthy improvement in PK variability as presented by CV % values for AUC and Cmax parameters for the soft gelatin capsules compared to the hard gelatin capsules in the study continued to be evident. The CV % for the soft gelatin were reduced to satisfactory levels of 42.1% and 43.1% for the AUC and Cmax respectively, from unacceptable CV % values of 64.7% and 69.3% respectively for the hard gelatin formulation.

Example 10. PK Study with Compound A Soft Gelatin Formulation in Healthy Human Post-Menopausal Women at Different Dose Levels The PK of Compound A after oral administration to healthy human post-menopausal women, was assessed in a Phase 1, open label, randomised, crossover study at four different dose levels utilising the new soft gelatin formulation. For this study however Compound A however was formulated as a 40 mg capsule according to Example 1a.

Study Protocol

Healthy human post-menopausal women were enrolled in the study consisting of 11-13 subjects in each of four cohorts that were assigned to one of four dose levels of Compound A formulated as a soft gelatin capsule as follows: Cohort 1, 40 mg (1 soft gelatin capsule); Cohort 2, 80 mg (2×40 mg capsules); Cohort 3, 120 mg (3×40 mg capsules); Cohort 4, 160 mg (4×40 mg capsules). Subjects were administered the capsule(s) in their respective cohorts as single doses on the morning of Day 1 after an overnight fast. Subjects then each received a single dose at their assigned levels for a further 7 days (Day 7) to achieve steady-state. Blood was sampled for assay of Compound A prior to dosing and post dose at both Days 1 and 7.

Results

As previously observed mean plasma Compound A concentrations increased rapidly, with median tmax at 1.0 to 1.5 hours post-dose for all four soft gelatin cohorts after single and repeat daily dosing. Cmax and AUC exposure PK data for all dose groups are shown after a single dose (Day 1 data) in Table 6 and repeated daily dosing (Day 7) in Table 7.

TABLE 6

Cmax and AUC values after a single oral administration on Day 1 for Compound A new soft gelatin capsule formulation according to the invention, at four different dose levels.

| Development Form | Anhydrous crystalline form (Form1) |
| --- | --- |
| Formulation | Soft gelatin capsule |
| Study population | Post-menopausal females |

TABLE 6-continued

Cmax and AUC values after a single oral administration on Day 1 for Compound A new soft gelatin capsule formulation according to the invention, at four different dose levels.

| Dose Cohort | | 40 mg | 80 mg | 120 mg | 160 mg |
|---|---|---|---|---|---|
| Number of 40 mg capsules | | 1 | 2 | 3 | 4 |
| | N | 12 | 13 | 11 | 12 |
| $AUC_{0-24}$ | Geometric mean (ng · hr/mL) | 1510 | 3780 | 7390 | 10400 |
| | CV % | 38.7 | 35.6 | 17.3 | 31.0 |
| Cmax | Geometric mean (ng/mL) | 549 | 1442 | 2541 | 3090 |
| | CV % | 42.4 | 51.9 | 25.6 | 37.8 |

TABLE 7

Cmax and AUC values after repeated daily oral administration on Day 7 for Compound A new soft gelatin capsule formulation according to the invention, at four different dose levels.

| Development Form | | Anhydrous crystalline form (Form1) | | | |
|---|---|---|---|---|---|
| Formulation | | Soft gelatin capsule | | | |
| Study population | | Post-menopausal females | | | |
| Dose Cohort | | 40 mg (1 × 40 mg capsule) | 80 mg (2 × 40 mg capsules) | 120 mg (3 × 40 mg capsules) | 160 mg (4 × 40 mg capsules) |
| | N | 12 | 13 | 11 | 12 |
| $AUC_{0-24}$ | Geometric mean (ng · hr/mL) | 2000 | 4950 | 9080 | 14100 |
| | CV % | 37.7 | 38.7 | 26.9 | 38.4 |
| Cmax | Geometric mean (ng/mL) | 525 | 1302 | 2053 | 2991 |
| | CV % | 37.7 | 37.5 | 45.7 | 36.9 |

A modest supra-proportional increase in exposure was observed with increasing dose level after single and repeat daily dosing. There is also a modest accumulation over the 7-day dosing period. What is remarkable however is the continued outstanding reduction in PK variability (CV % values) both for AUC and Cmax parameters after a single dose for the soft gelatin capsules (Table 6); that is notably sustained on repeated daily dosing (Table 7). The reduced CV % values attained at steady-state after 7-days repeated once-daily dosing with the soft gelatin formulation are even more remarkable as they were obtained despite multiples of the 40 mg soft gelatin capsule being administered to subjects each day for the 80, 120 and 160 mg doses. The 160 mg dose for instance required 4×40 mg capsules. The improved levels of the key parameter of PK variability achieved with the soft gelatin capsule formulation compared to that for the solid dose hard gelatin capsule is fully evident as shown in Example 11.

An improvement in the other key PK parameter of bioavailability was also observed with the soft gelatin capsules versus the hard gelatin capsules. The exposure achieved with the once-a-day 80 mg of Compound A in the soft gelatin capsules at steady-state was similar to that achieved with the 'maximal efficacy' 150 mg dose of Compound A in the hard gelatin capsule in the Phase 1b/2 clinical trial in post-menopausal women suffering moderate to severe vasomotor symptoms described (Table 8), demonstrating that the desired level of therapeutic exposure can be achieved with the discovered soft gelatin formulation These data also once more demonstrate the improved PK variability with the soft gelatin capsule formulation versus the hard gelatin capsule, as evidenced by the reduced CV % value of 38.7% versus unacceptable 97.8% respectively.

TABLE 8

Comparison of doses that gave similar exposures from repeated daily oral administration of Compound A new soft gelatin capsule formulation according to the invention versus the hard gelatin capsule of Table 2.

| Compound | Anhydrous crystalline form (Form1) | |
|---|---|---|
| Study population | Post-menopausal females | |
| Formulation | Soft Gelatin Capsule | Hard Gelatin Capsule |
| Study | Phase 1 | Phase 1b/2 |
| Dose Cohort | 80 mg (2 × 40 mg capsules (Example 1a)) | 150 mg (3 × 50 mg capsules) |
| | N | 13 | 15 |
| $AUC_{0-tau}$ | Geometric mean (ng · hr/mL) | 4950 | 5164 |
| | CV % | 38.7 | 97.8 |

The improvement in bioavailability observed with the soft gelatin capsule indicates that the amount of Compound A required to be formulated for efficacy is expected to be decreased by nearly 50% compared to the hard gelatin formulation, giving an additional advantage of a lower cost of goods to manufacture this drug substance.

Example 11. Demonstration of the Reduced Variability in Repeat Dose Studies with Soft Gelatin Capsule Formulation Versus Solid Dose Hard Gelatin Capsule Formulation Steady-state minimum and maximum PK values (Cmax and $AUC_{0-24}$) and their ratios to each other, from the Phase 1b/2 clinical study in post-menopausal women involving repeated dosing of the hard gelatin capsule formulation of Compound A anhydrous crystalline form (Form 1) (see Table 3 for formulation), and the Phase 1 study described in Example 10 involving repeated dosing at 4 different dose levels of the soft gelatin capsule in the same subject population, are listed in Table 9, together with geometric means and CV % values.

TABLE 9

Steady-state PK data from repeat dose studies with soft gelatin and hard gelation capsules in post-menopausal females showing minimum and maximum values and their ratio to each other and CV % values
Development Form: Anhydrous crystalline form (Form1)
Study populations: Post-menopausal females

| Formulation | PK parameter | Dose (mg) | N | Geometric Mean | CV % | Minimum (Min) | Maximum (Max) | Ratio (Max:Min) |
|---|---|---|---|---|---|---|---|---|
| Hard gelatin capsule doses | Cmax (ng/mL) | 50 | 15 | 522 | 87.9 | 142 | 1544 | 10.9 |
| | | 100 | 14 | 841 | 107.2 | 181 | 3856 | 21.3 |
| | | 150 | 15 | 1188 | 131.2 | 208 | 5903 | 28.4 |

TABLE 9-continued

Steady-state PK data from repeat dose studies with soft gelatin and hard
gelation capsules in post-menopausal females showing minimum and maximum values and
their ratio to each other and CV % values
Development Form: Anhydrous crystalline form (Form1)
Study populations: Post-menopausal females

| Formulation | PK parameter | Dose (mg) | N | Geometric Mean | CV % | Minimum (Min) | Maximum (Max) | Ratio (Max:Min) |
|---|---|---|---|---|---|---|---|---|
| Steady-state Day 14 | $AUC_{0-24}$ (ng · hr/mL) | 300 | 13 | 2852 | 116.5 | 237 | 8653 | 36.5 |
| | | 50 | 15 | 2342 | 64.7 | 915 | 5540 | 6.1 |
| | | 100 | 14 | 3542 | 86.3 | 778 | 10938 | 14.1 |
| | | 150 | 15 | 5164 | 88.7 | 1564 | 16163 | 10.3 |
| | | 300 | 13 | 14823 | 99.7 | 2457 | 79685 | 32.4 |
| Soft gelatin capsule doses Steady-State Day 7 | Cmax (ng/mL) | 40 | 12 | 525 | 37.7 | 294 | 926 | 3.1 |
| | | 80 | 12 | 1302 | 37.5 | 669 | 2190 | 3.3 |
| | | 120 | 11 | 2053 | 45.7 | 840 | 4320 | 5.1 |
| | | 160 | 12 | 2991 | 36.9 | 1910 | 5780 | 3.0 |
| | $AUC_{0-24}$ (ng · hr/mL) | 40 | 12 | 2000 | 37.7 | 1050 | 3700 | 3.5 |
| | | 80 | 12 | 4950 | 38.7 | 3180 | 9200 | 2.9 |
| | | 120 | 11 | 9080 | 26.9 | 4730 | 11200 | 2.4 |
| | | 160 | 12 | 14100 | 38.4 | 8520 | 29000 | 3.4 |

The minimum and maximum ratio PK parameter data exhibited in Table 9 verifies the remarkable and surprising reduction in variability of the soft gelatin formulation of Compound A according to the invention compared to the solid dose hard gelatin formulation. This superiority is evident from the lower ratios for the PK parameters for the soft gelatin capsules that range from only 2.9 to 5.1, while for the hard gelatin capsules values range from 6.1 to 36.5; likewise the lower CV % values for the soft gelatin capsules that range from an acceptable level of 26.9% to 45.7% compared to 64.7% to 131.2% for the hard gelatin capsules.

These data together with the demonstration that therapeutic exposures of Compound A can be achieved, confirm that the soft gelatin formulation of Compound A according to the invention is fully suitable for further development from a PK parameter perspective.

Example 12. Studies Demonstrating Good Stability of Soft Gelatin Formulations The third key test that needed to be met was to demonstrate good long term stability of the discovered soft gelatin capsule formulation. Soft gelatin capsules that were produced using the compositions described in Examples 1.1 and 1a, were evaluated in a stability chamber under accelerated stability conditions namely 40° C./75% Relative Humidity. The soft gelatin capsules from Example 1.1 were put down on stability in high-density polyethylene (HDPE) bottles. Those in Example 1a were packed in alu:alu blisters. Both soft gelatin capsule formulations showed good stability as shown by the limited amount of total impurities in Example 1.1 out to 6 months and for Example 1a out to 3 months in which no impurities could be detected, under these accelerated stability conditions.

TABLE 10

Assay results for Compound A formulated as soft gelatin capsules under accelerated stability conditions

| | Stability Time Point | | | | | | | |
|---|---|---|---|---|---|---|---|---|
| | Time Zero | | 1 month | | 3 months | | 6 months | |
| Soft gelatin formulation | Label claim % | Total impurities % | Label claim % | Total impurities % | Label claim % | Total impurities % | Label claim % | Total impurities % |
| Example 1.1 | 103.4 | 0.1 | 103.0 | 0.3 | 100.8 | 0.2 | 101.1 | 0.2 |
| Example 1a | 99.2 | LTLOQ | 99.6 | LTLOQ | 98.6 | LTLOQ | DNA | DNA |

Key:
LTLOQ—Less than the limit of quantitation;
DNA—data not yet available

Examination of the soft gelatin capsules from these studies also showed no evidence of recrystallization, precipitation, nor phase separation.

Therefore Compound A formulated as soft gelatin capsules demonstrated remarkably good stability under these accelerated stability environment indicating the suitability of these compositions for manufacture, distribution and long term storage under ambient conditions.

These remarkable PK and stability data confirm that the unexpectedly discovered novel formulations of Compound A according to the invention are fully suitable for further clinical development.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

The invention claimed is:

1. A method of treating sleep disturbances associated with menopause, or night time awakenings associated with menopause, or both, in a human in need thereof, the method comprising administering to the human a daily dose of 100 mg to 160 mg of 2-[3,5-bis(trifluoromethyl)phenyl]-N-{4-(4-fluoro-2-methylphenyl)-6-[(7S,9aS)-7-(hydroxymethyl) hexahydropyrazino[2,1-c][1,4]oxazin-8(1H)-yl]-3-pyridinyl}-N,2-dimethylpropanamide (Compound A):

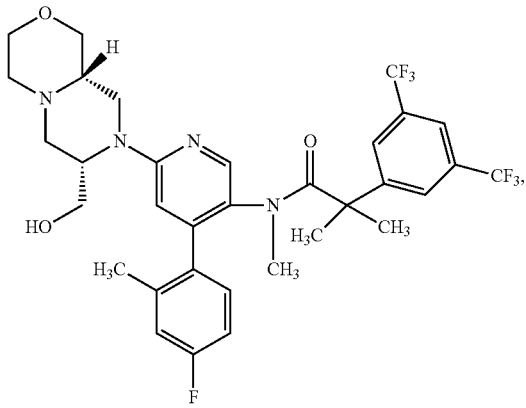

(Compound A)

or a pharmaceutically acceptable salt thereof.

2. The method of claim 1, wherein Compound A is in a crystalline anhydrate form.

3. The method of claim 1, wherein the Compound A is in crystalline anhydrate Form 1, characterized by X-ray powder diffraction (XRD) pattern expressed in terms of 2 theta angles, wherein the XRD pattern comprises 2 theta angle peaks at 4.3±0.1, 7.9±0.1, 9.8±0.1, 10.7±0.1, 10.8±0.1, 13.3±0.1, 14.0±0.1, 15.1±0.1 degrees, which correspond respectively to d-spacing at 20.4, 11.1, 9.0, 8.3, 8.2, 6.6, 6.3 and 5.9 Angstroms (Å).

4. The method of claim 1, further comprising administering to the human one or more additional therapeutic agents.

5. The method of claim 1, wherein Compound A is administered to the human in one or more soft gelatin capsules, wherein each soft gelatin capsule comprises:
Compound A or a pharmaceutically acceptable salt thereof;
at least one solubilizer selected from the group consisting of caprylocaproyl polyoxyl-8 glycerides, glycerol monocaprylocaprate, polyoxyl 35 castor oil, and polysorbate 80, or any mixtures thereof; and
at least one antioxidant selected from the group consisting of dl-alpha-tocopherol, butylated hydroxytoluene, and butylated hydroxyanisole or any mixtures thereof.

6. The method of claim 5, wherein the soft gelatin capsule further comprises at least one emulsifier.

7. The method of claim 5, wherein the soft gelatin capsule comprises 10 mg to 80 mg of Compound A.

8. The method of claim 6, wherein the soft gelatin capsule comprises 10 mg to 80 mg of Compound A.

9. The method of claim 5, wherein the soft gelatin capsule comprises Compound A at a concentration ranging from 0.8% w/w to 15% w/w or from 5% w/w to 10% w/w.

10. The method of claim 6, wherein the soft gelatin capsule comprises Compound A at a concentration ranging from 0.8% w/w to 15% w/w or from 5% w/w to 10% w/w.

11. The method of claim 5, wherein at least one solubilizer is glycerol monocaprylocaprate, caprylocaproyl polyoxyl-8 glycerides, or polysorbate 80.

12. The method of claim 6, wherein at least one solubilizer is glycerol monocaprylocaprate, caprylocaproyl polyoxyl-8 glycerides, or polysorbate 80.

13. The method of claim 6, wherein at least one emulsifier is glyceryl monooleate.

14. The method of claim 5, wherein at least one antioxidant is dl-alpha-tocopherol.

15. The method of claim 6, wherein at least one antioxidant is dl-alpha-tocopherol.

16. The method of claim 1, wherein Compound A is administered to the human in one or more soft gelatin capsules, wherein each soft gelatin capsule comprises:
Compound A;
glycerol monocaprylocaprate;
caprylocaproyl polyoxyl-8-glycerides;
polysorbate 80; and
dl-alpha-tocopherol.

17. The method of claim 16, wherein each soft gelatin capsule further comprises:
glyceryl monooleate.

18. The method of claim 11, wherein glycerol monocaprylocaprate is present in each soft gelatin capsule at a concentration ranging from 20% w/w to 65% w/w.

19. The method of claim 12, wherein glycerol monocaprylocaprate is present in each soft gelatin capsule at a concentration ranging from 20% w/w to 65% w/w.

20. The method of claim 11, wherein caprylocaproyl polyoxyl-8 glycerides is present in each soft gelatin capsule at a concentration ranging from 7% w/w to 13% w/w.

21. The method of claim 12, wherein caprylocaproyl polyoxyl-8 glycerides is present in each soft gelatin capsule at a concentration ranging from 7% w/w to 13% w/w.

22. The method of claim 11, wherein polysorbate 80 is present in each soft gelatin capsule at a concentration from 7% w/w to 13% w/w.

23. The method of claim 12, wherein polysorbate 80 is present in each soft gelatin capsule at a concentration from 7% w/w to 13% w/w.

24. The method of claim 13, wherein glyceryl monooleate is present in each soft gelatin capsule at a concentration ranging from 15% w/w to 60% w/w.

25. The method of claim 14, wherein dl-alpha-tocopherol is present in each soft gelatin capsule at a concentration ranging from 0.05% w/w to 1.5% w/w.

26. The method of claim 15, wherein dl-alpha-tocopherol is present in each soft gelatin capsule at a concentration ranging from 0.05% w/w to 1.5% w/w.

27. The method of claim 1, wherein Compound A is administered to the human in one or more soft gelatin capsules, wherein each soft gelatin capsule comprises:
Compound A present at a concentration ranging from 5% w/w to 10% w/w;
glycerol monocaprylocaprate present at a concentration ranging from 20% w/w to 65% w/w;
caprylocaproyl polyoxyl-8 glycerides present at a concentration ranging from 7% w/w to 13% w/w;
polysorbate 80 present at a concentration from 7% w/w to 13% w/w;
dl-alpha-tocopherol present at a concentration ranging from 0.5% w/w to 1% w/w; and
glyceryl monooleate.

28. The method of claim 27, wherein each soft gelatin capsule is prepared by a method comprising adding Compound A to a mixture comprising 15% w/w to 60% w/w glyceryl monooleate, glycerol monocaprylocaprate, caprylocaproyl polyoxyl-8 glycerides, polysorbate 80, or dl-alpha-tocopherol.

29. The method of claim 1, wherein Compound A is administered to the human in one or more soft gelatin capsules, wherein each soft gelatin capsule comprises:
   Compound A present at a concentration ranging from 5% w/w to 10% w/w;
   glycerol monocaprylocaprate present at a concentration ranging from 20% w/w to 65% w/w;
   caprylocaproyl polyoxyl-8 glycerides present at a concentration ranging from 7% w/w to 13% w/w;
   polysorbate 80 present at a concentration from 7% w/w to 13% w/w;
   dl-alpha-tocopherol present at a concentration ranging from 0.5% w/w to 1% w/w; and
   glyceryl monooleate present at a concentration ranging from 15% w/w to 60% w/w.

30. The method of claim 1, wherein Compound A is administered to the human in one or more soft gelatin capsules, wherein each soft gelatin capsule comprises:
   Compound A present at a concentration ranging from 1% w/w to 10% w/w;
   glycerol monocaprylocaprate present at a concentration ranging 30% w/w to 40% w/w;
   caprylocaproyl polyoxyl-8 glycerides present at a concentration ranging from 7% w/w to 13% w/w;
   polysorbate 80 present at a concentration from 7% w/w to 13% w/w;
   dl-alpha-tocopherol present at a concentration ranging from 0.5% w/w to 1% w/w; and
   glyceryl monooleate.

31. The method of claim 30, wherein each soft gelatin capsule is prepared by a method comprising adding Compound A to a mixture comprising 33% w/w to 43% w/w glyceryl monooleate, glycerol monocaprylocaprate, caprylocaproyl polyoxyl-8 glycerides, polysorbate 80, or dl-alpha-tocopherol.

32. The method of claim 1, wherein Compound A is administered to the human in one or more soft gelatin capsules, wherein each soft gelatin capsule comprises:
   Compound A present at a concentration ranging from 5% w/w to 10% w/w;
   glycerol monocaprylocaprate present at a concentration ranging from 20% w/w to 65% w/w;
   caprylocaproyl polyoxyl-8 glycerides present at a concentration ranging from 7% w/w to 13% w/w;
   polysorbate 80 present at a concentration from 7% w/w to 13% w/w;
   dl-alpha-tocopherol present at a concentration ranging from 0.5% w/w to 1% w/w; and
   glyceryl monooleate present at a concentration ranging from 33% w/w to 43% w/w.

33. The method of claim 1, wherein Compound A is administered at a daily dose of 120 mg.

34. The method of claim 6, wherein at least one emulsifier is glyceryl monooleate, or Miglyol 812, or a mixture thereof.

* * * * *